US009359336B2

(12) United States Patent
Boral et al.

(10) Patent No.: US 9,359,336 B2
(45) Date of Patent: Jun. 7, 2016

(54) HETEROCYCLE-SUBSTITUTED PYRIDYL BENZOTHIOPHENES AS KINASE INHIBITORS

(71) Applicant: Allergan, Inc., Irvine, CA (US)

(72) Inventors: Sougato Boral, Irvine, CA (US); Thomas C. Malone, Irvine, CA (US); Shimiao Wang, Tustin, CA (US); Sandhya Rao, Irvine, CA (US); Rong Yang, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/511,004

(22) Filed: Oct. 9, 2014

(65) Prior Publication Data

US 2016/0102081 A1 Apr. 14, 2016

(51) Int. Cl.
*C07D 409/14* (2006.01)
*C07D 405/14* (2006.01)
*C07D 401/04* (2006.01)

(52) U.S. Cl.
CPC ............ *C07D 409/14* (2013.01); *C07D 401/04* (2013.01); *C07D 405/14* (2013.01)

(58) Field of Classification Search
CPC ..................................................... C07D 409/14
USPC ....................................... 546/268.4; 514/337
See application file for complete search history.

(56) References Cited

U.S. PATENT DOCUMENTS

| | | | |
|---|---|---|---|
| 3,536,809 | A | 10/1970 | Applezwig |
| 3,598,123 | A | 8/1971 | Zaffaroni et al. |
| 3,630,200 | A | 12/1971 | Higuchi et al. |
| 3,845,770 | A | 11/1974 | Higuchi et al. |
| 3,916,899 | A | 11/1975 | Higuchi et al. |
| 4,008,719 | A | 2/1977 | Theeuwes et al. |
| 5,366,738 | A | 11/1994 | Rork et al. |
| 7,037,916 | B2 | 5/2006 | Erickson et al. |
| 8,648,201 | B2 | 2/2014 | Calderini et al. |
| 2009/0197862 | A1 | 8/2009 | Steinig et al. |
| 2012/0115861 | A1 | 5/2012 | Calderini et al. |

FOREIGN PATENT DOCUMENTS

| | | | |
|---|---|---|---|
| DE | 102009033208 | A1 | 1/2011 |
| KR | 2011033395 | A | 3/2011 |
| WO | 99-62890 | | 12/1999 |
| WO | 2005-082001 | | 9/2005 |
| WO | 2006-026034 | | 3/2006 |
| WO | 2009053737 | A3 | 4/2009 |
| WO | 2009126003 | A3 | 10/2009 |
| WO | 2011006567 | A1 | 1/2011 |

OTHER PUBLICATIONS

Dorwald , Side Reactions in Organic Synthesis, 2005, Wiley: VCH Weinheim Preface, pp. 1-15 & Chapter 8, pp. 279-308.*

Nobuo Jo, Carolina Mailhos,et al., Inhibition of Platelet-Derived Growth Factor B Signaling Enhances the Efficacy of Anti-Vascular Endothelial Growth Factor Therapy in Multiple Models of Ocular Neovascularization, American Journal of Pathology, vol. 168, No. 6, Jun. 2006.

Justine R Smith, et al., Expression of vascular endothelial growth factor and its receptors in rosacea, Br J Ophthalmol 2007;91:226-229. doi: 10.1136/bjo.2006.101121.

S. W. Cowan-Jacob, et al., Structural biology of protein tyrosine kinases, Cell. Mol. Life Sci. 63 (2006) 2608-2625.

Regina Heidenreich, et al., Angiogenesis: The New Potential Target for the Therapy of Psoriasis?Drug News Perspect 21(2), Mar. 2008.

Aimee V. Chappelow et al., Neovascular Age-Related Macular Degeneration, Potential Therapies, Drugs 2008; 68 (8): 1029-1036.

Mark Rami Barakat, et al., VEGF inhibitors for the treatment of neovascular age-related macular degeneration, Expert Opin. Investig. Drugs (2009) 18(5).

Xinyuan Zhang, et al., Vascular endothelial growth factor-A: A multifunctional molecular player in diabetic retinopathy, The International Journal of Biochemistry & Cell Biology 41 (2009) 2368-2371.

Zhang Ni, et al., Emerging Pharmacologic Therapies for Wet Age-Related Macular Degeneration, Ophthalmologica 2009;223:401-410.

Jayne M. Stommel et al., Coactivation of Receptor Tyrosine Kinases Affects the Response of Tumor Cells to Targeted Therapies, www.sciencemag.org, Science vol. 318 Oct. 12, 2007.

Akulapalli Sudhakar et al., Phosphorylation of Serine 51 in Initiation Factor 2α (elF2α) Promotes Complex Formation between elF2α(P) and elF2B and Causes Inhibition in the Guanine Nucleotide Exchange Activity of elF2B†, Biochemistry 2000, 39, 12929-12938.

Madhusudan Dey et al., Mechanistic Link between PKR Dimerization, Autophosphorylation, and elF2α Substrate Recognition, Cell, vol. 122, 901-913, Sep. 23, 2005.

Neysan Donnelly et al., The elF2α kinases: their structures and functions, Cell. Mol. Life Sci. (2013) 70:3493-3511.

Qiaozhu Su et al., Interferons induce tyrosine phosphorylation of the elF2α kinase PKR through activation of Jak1 and Tyk2, EMBO reports vol. 8, No. 3, 2007.

Masamitsu Shimazawa et al., Involvement of Double-Stranded RNA-Dependent Protein Kinase in ER Stress-Induced Retinal Neuron Damage, IOVS, Aug. 2007, vol. 48, No. 8.

(Continued)

*Primary Examiner* — Patricia L Morris
(74) *Attorney, Agent, or Firm* — Jonathan Bass

(57) ABSTRACT

This invention is directed to a compound of Formula I

Formula I

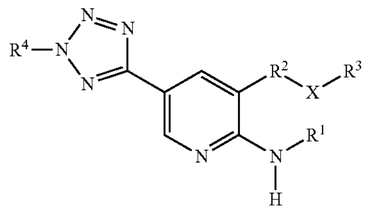

or a pharmaceutically acceptable salt thereof, wherein $R^1$, $R^2$, $R^3$, $R^4$ and X are as defined herein. The compounds of Formula I are useful as receptor tyrosine kinase (RTK) inhibitors and can be used to treat such diseases as cancer, blood vessel proliferative disorders, fibrotic disorders, mesangial cell proliferative disorders and metabolic diseases.

8 Claims, No Drawings

(56) References Cited

OTHER PUBLICATIONS

Silva et al., Protein Kinase R (PKR) Interacts with and Activates Mitogen-activated Protein Kinase Kinase 6 (MKK6) in Response to Double-stranded RNA Stimulation, J. Biol. Chem. 2004, 279:37670-37676.
Howard C.H. Yim et al., Protein Kinase R and the Inflammasome, Journal of Interferon & Cytokine Research, vol. 34, No. 6, 2014.
Matthew Campbell et al., An eye on the future of inflammasomes and drug development in AMD, J Mol Med (2013) 91:1059-1070.
M. A. Garcia et al., Impact of Protein Kinase PKR in Cell Biology: from Antiviral to Antiproliferative Action, Microbiol. Mol. Biol, Rev. 2006, 70(4):1032.
Ben Lu et al., Novel role of PKR in inflammasome activation and HMGB1 release, Nature. Aug. 30, 2012; 488 (7413): 670-674, www.nature.com/nature.
Siddharth Balachandran et al., Activation of the dsRNA-dependent protein kinase, PKR, induces apoptosis through FADD-mediated death signaling, The EMBO Journal vol. 17 No. 23 pp. 6888-6902, 1998.
Goh et al., The protein kinase PKR is required for p38 MAPK activation and the innate immune response to bacterial endotoxin, The EMBO Journal vol. 19 No. 16 pp. 4292-4297, 2000.
Arora, A., et al., Role of Tyrosine Kinase Inhibitors in Cancer Therapy, The Journal of Pharmacology and Experimental Therapeutics 2005, 315: 971-919 (3).
Bergers, G. et al., Benefits of targeting both pericytes and endothelial cells in the tumor vasculature with kinase inhibitors, The Journal of Clinical Investigation 2003, 111: 1287-1295 (9).
Cross, L.C., et al., Rules for the Nomenclature of Organic Chemistry, Section E: Stereochemistry, Pure & Applied Chemistry 1976, 45: 11-30.
Stahl, Heinrich, et al., Handbook of Pharmaceutical Salts: Properties, Selection, and Use, 2002, pp. 1-19.

* cited by examiner

HETEROCYCLE-SUBSTITUTED PYRIDYL BENZOTHIOPHENES AS KINASE INHIBITORS

FIELD OF THE INVENTION

The invention relates to inhibitors of vascular endothelial growth factor receptor 2 kinase (VEGFR2) or VEGFR, platelet derived growth factor beta (PDGFRβ) kinases or PDGFR and Protein Kinase R (EIF2AK2), and methods of using such compounds. The present invention is also directed to methods of regulating, modulating or inhibiting protein kinases, whether of the receptor or non-receptor class, for the prevention and/or treatment of disorders related to unregulated protein kinase signal transduction, including cell growth, metabolic, blood vessel proliferative, inflammatory and neurodegenerative disorders.

DESCRIPTION OF THE RELATED ART

Protein kinases (PKs) comprise a large and diverse class of proteins having enzymatic activity which catalyzes the transfer of the terminal phosphate of ATP to the hydroxyl group of a serine, threonine or tyrosine group in a protein. Protein kinases (PKs) are involved in numerous diseases which result from dysregulation of their normal function.

There are numerous examples where protein kinases, have been found to be involved in cellular signaling pathways leading to pathological conditions. In the VEGFR2 kinase protein kinase, which is a receptor tyrosine kinase, pathological conditions involving aberrant angiogenesis include cancer, wet age-related macular degeneration (Ni et al. Opthalmologica 2009 223 401-410; Chappelow et al. Drugs 2008 68 1029-1036), diabetic retinopathy (Zhang et al Int. J. Biochem. Cell Biol. 2009 41 2368-2371), cancer (Aora et al. J. Path. Exp. Ther. 2006, 315, 971), psoriasis (Heidenreich et al Drug News Perspective 2008 21 97-105) and hyper immune response. In ophthalmic diseases such as neovascular age-related macular degeneration and diabetic retinopathy aberrant activation of VEGF receptors can lead to abnormal blood vessel growth. The importance of VEGFR signaling in the neovascular age-related macular degeneration disease process is evident by the clinical success of multiple anti-VEGF targeting agents including Lucentis®, Avastin®, and EYLEA™ (Barakat et al. Expert Opin. Investig. Drugs 2009, 18, 637). Recently it has been suggested that inhibition of multiple protein kinase signaling pathways may provide a greater therapeutic effect than targeting a single signaling pathway. For example in neovascular ocular disorders such as neovascular age-related macular degeneration and diabetic retinopathy the inhibition of both VEGFR and PDGFRβ may provide a greater therapeutic effect in by causing regression of existing neovascular blood vessels present in the disease (Adamis et al. Am. J. Pathol. 2006 168 2036-2053). In cancer inhibition of multiple PK signaling pathways has been suggested to have a greater effect than inhibiting a single PK pathway (DePinho et al. Science 2007 318 287-290; Bergers et al. J. Clin Invest. 2003 111 1287-1295).

It has also been suggested that misregulated protein kinases are involved in neurodegenerative disease. In particular Protein Kinase R has been implicated in neurodegenerative disease. Protein Kinase R (PKR, also known as interferon-induced, double-stranded RNA-activated protein kinase, or eukaryotic translation initiation factor 2-alpha kinase 2) is one of four known mammalian kinases that phosphorylate eukaryotic translation initiation factor 2-alpha (eIF-2α) in response to a variety of stress conditions (Donnelly et al., Cell. Mol. Life Sci. 2013, 70, 3493-3511). PKR plays a central role in the innate immune system and serves to prevent viral replication and viral infection (for a detailed review see Garcia et al., Microbiol. and Mol. Bio. Rev. 2006, 70, 1032-1060). It is proposed that in chronic conditions like AMD, innate immune players respond to modified host derived elements (ROS/Alu) and external particulate matter (drusen) by activation of inflammasome complex. Emerging evidence indicates that PKR has a key role in NLRP3 inflammasome activation (Yim & Williams; J of Interferon & Cytokine Res, 2014, Campbell & Doyle, J Mol Med, 2013, Lu et. al; Nature, 2012).

The binding of double stranded RNA to the double stranded RNA regulatory domains of PKR induces dimerization and autophosphorylation which leads to activation of the kinase (Dever et al., Cell 2005, 122, 901-913). Once activated by dimerization PKR can suppress protein synthesis by phosphorylation of serine-51 on eukaryotic translation initiation factor 2-alpha (eIF-2α). In its phosphorylated form eIF2alpha increases its affinity for eIF-2B by 100-fold effectively converting it into a competitive inhibitor of eIF-2B. By this mechanism a small amount of phosphorylated eIF2alpha can effectively inhibit the guanine nucleotide exchange activity of eIF-2B and shut down protein translation (Ramaiah et al., Biochemistry 2000, 39, 12929-12938).

In addition to PKR's role in regulation of protein synthesis it also plays an important role in signal transduction linked to apoptotic cell death. PKR has been shown to be activated by dsRNA, number of growth factors and cytokines including INF, PDGF, TNF-alpha, and IL-1 and by the activation of Toll receptors. PKR has also been shown to be phosphorylated by JAK1 and Tyk2 kinases (Su et al., EMBO Reports 2007, 3, 265). Activation of PKR leads to the activation of multiple signaling pathways that are involved in inflammation and cell death. PKR is required for phosphorylation of MKK6 (Williams et al., J. Biol. Chem. 2004, 279, 37670-37676) and subsequent p38 MAPK signaling (Williams et al., The EMBO Journal 2000, 19, 4292-4297). PKR induces the expression of the pro apoptotic factor CHOP and has been shown to induce apoptosis by the FADD/Caspase 8 pathway (Barber, G. et al, The EMBO Journal 1998, 17, 6888-6902).

Due to its key role in regulation of apoptotic cell death PKR inhibition may be useful in prevention of the rod and cone photoreceptor cell death and ganglion cell death associated with the atrophic form of macular degeneration (Shimazawa et al, IVOS 2007, 48, 3729-3736).

The identification of effective small compounds which specifically inhibit signal transduction by modulating the activity of receptor and non-receptor protein kinases to regulate and modulate abnormal or inappropriate cell proliferation is therefore desirable and one object of this invention.

Certain small compounds are disclosed in PCT publication No. WO/1999/062890, PCT publication No. WO/2005/082001 and PCT publication No. WO/2006/026034 as useful for the treatment of diseases related to unregulated TKS transduction.

SUMMARY OF THE INVENTION

The present invention relates to organic molecules capable of modulating, regulating and/or inhibiting tyrosine kinase signal transduction by blocking the VEGF and/or PDGF receptors. Such compounds are useful for the treatment of diseases related to unregulated PTKs transduction, including cell proliferative diseases such as cancer; vascular (blood vessel) proliferative disorders such as mesangial cell proliferative disorders and metabolic diseases, lung carcinomas, breast carcinomas, Non Hodgkin's lymphomas, ovarian carcinoma, pancreatic cancer, malignant pleural mesothelioma, melanoma, arthritis, restenosis, hepatic cirrhosis, atherosclerosis, psoriasis, rosacea, diabetic mellitus, wound healing and inflammation and preferably ophthalmic diseases, i.e. diabetic retinopathy, retinopathy of prematurity, macular edema, retinal vein occlusion, exudative or neovascular age-related macular degeneration, high-risk eyes (i.e. fellow eyes have neovascular age-related macular degeneration) with dry age-related macular degeneration, neovascular disease associated with retinal vein occlusion, neovascular disease (including choroidal neovascularization) associated with the following: pathologic myopia, pseudoxanthoma elasticum, optic nerve drusen, traumatic choroidal rupture, central serous retinopathy, cystoid macular edema, diabetic retinopathy, proliferative diabetic retinopathy, diabetic macular edema, rubeosis iridis, retinopathy of prematurity, Central and branch retinal vein occlusions, inflammatory/infectious retinal, neovascularization/edema, corneal neovascularization, hyperemia related to an actively inflamed pterygia, recurrent pterygia following excisional surgery, post-excision, progressive pterygia approaching the visual axis, prophylactic therapy to prevent recurrent pterygia, of post-excision, progressive pterygia approaching the visual axis, chronic low grade hyperemia associated with pterygia, neovascular glaucoma, iris neovascularization, idiopathic etiologies, presumed ocular histoplasmosis syndrome, retinopathy of prematurity, chronic allergic conjunctivitis, ocular rosacea, blepharoconjunctivitis, recurrent episcleritis, keratoconjunctivitis sicca, ocular graft vs host disease, etc.

In one aspect, the invention provides a compound represented by Formula I or a pharmaceutically acceptable salt thereof or stereoisomeric forms thereof, or the enantiomers, diastereoisomers, tautomers, zwitterions and pharmaceutically acceptable salts thereof:

Formula I

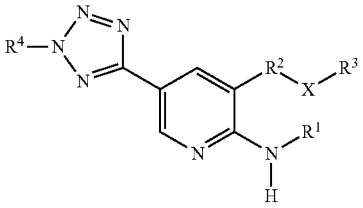

wherein:

$R^1$ is hydrogen, substituted or unsubstituted $C_1$-$C_8$ alkyl;

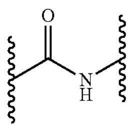,
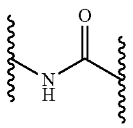
or
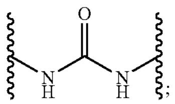

$R^2$ is substituted or unsubstituted heterocycle,

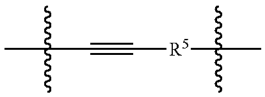

or substituted or unsubstituted aryl;

$R^3$ is substituted or unsubstituted heterocycle, substituted or unsubstituted aryl, $R^4$ is hydrogen or substituted or unsubstituted $C_1$-$C_8$ alkyl; and $R^5$ is substituted or unsubstituted heterocycle or substituted or unsubstituted aryl.

In another aspect, the invention provides a compound represented by Formula I wherein:

$R^1$ is hydrogen, substituted or unsubstituted $C_1$-$C_8$ alkyl;

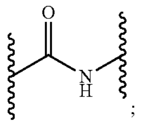 [SMILES: *NC(*)=O]

$R^2$ is substituted or unsubstituted heterocycle,

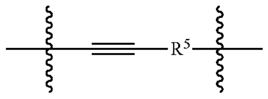

or substituted or unsubstituted aryl;

$R^3$ is substituted or unsubstituted heterocycle, substituted or unsubstituted aryl, $R^4$ is hydrogen or substituted or unsubstituted $C_1$-$C_8$ alkyl; and $R^5$ is substituted or unsubstituted heterocycle or substituted or unsubstituted aryl.

In another aspect, the invention provides a compound represented by Formula I wherein:

$R^1$ is hydrogen, substituted or unsubstituted $C_1$-$C_8$ alkyl;

X is

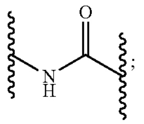 [SMILES: *NC(*)=O]

$R^2$ is substituted or unsubstituted heterocycle,

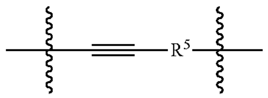

or substituted or unsubstituted aryl;

$R^3$ is substituted or unsubstituted heterocycle, substituted or unsubstituted aryl, $R^4$ is hydrogen or substituted or unsubstituted $C_1$-$C_8$ alkyl; and $R^5$ is substituted or unsubstituted heterocycle or substituted or unsubstituted aryl.

In another aspect, the invention provides a compound represented by Formula I wherein:

$R^1$ is hydrogen, substituted or unsubstituted $C_1$-$C_8$ alkyl;

X is

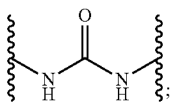 [SMILES: *NC(=O)N*]

$R^2$ is substituted or unsubstituted heterocycle,

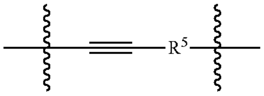

or substituted or unsubstituted aryl;

$R^3$ is substituted or unsubstituted heterocycle, substituted or unsubstituted aryl, $R^4$ is hydrogen or substituted or unsubstituted $C_1$-$C_8$ alkyl; and $R^5$ is substituted or unsubstituted heterocycle or substituted or unsubstituted aryl.

In another aspect, the invention provides a compound represented by Formula I wherein:

$R^1$ is hydrogen;

X is

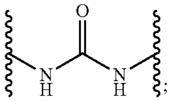 [SMILES: *NC(=O)N*];

$R^2$ is substituted or unsubstituted heterocycle;

$R^3$ is substituted or unsubstituted aryl, $R^4$ is hydrogen or substituted or unsubstituted $C_1$-$C_8$ alkyl.

In another aspect, the invention provides a compound represented by Formula I wherein:

$R^1$ is hydrogen;

X is

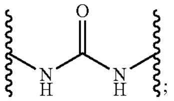 [SMILES: *NC(=O)N*];

$R^2$ is substituted or unsubstituted heterocycle;

$R^3$ is substituted or unsubstituted aryl, $R^4$ is hydrogen.

In another aspect, the invention provides a compound represented by Formula I wherein:

$R^1$ is hydrogen;

X is

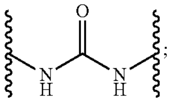 [SMILES: *NC(=O)N*];

$R^2$ is substituted or unsubstituted heterocycle;

$R^3$ is substituted or unsubstituted aryl, $R^4$ is substituted or unsubstituted $C_1$-$C_8$ alkyl.

In another aspect, the invention provides a compound represented by Formula I wherein:

$R^1$ is hydrogen;

X is

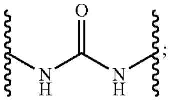 [SMILES: *NC(=O)N*];

$R^2$ is

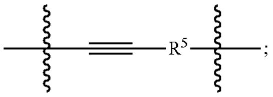;

$R^3$ is substituted or unsubstituted aryl, $R^4$ is substituted or unsubstituted $C_1$-$C_8$ alkyl; and $R^5$ is substituted or unsubstituted aryl.

In another aspect, the invention provides a compound represented by Formula I wherein:

$R^1$ is hydrogen;

X is

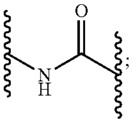 [SMILES: *NC(*)=O];

$R^2$ is

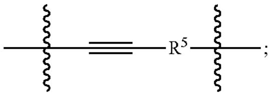;

$R^3$ is substituted or unsubstituted heterocycle, substituted or unsubstituted aryl, $R^4$ is substituted or unsubstituted $C_1$-$C_8$ alkyl; and $R^5$ is substituted or unsubstituted aryl.

In another aspect, the invention provides a compound represented by Formula I wherein:

$R^1$ is hydrogen;

X is

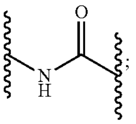 [SMILES: *NC(*)=O];

$R^2$ is substituted or unsubstituted heterocycle;

$R^3$ is substituted or unsubstituted heterocycle, substituted or unsubstituted aryl; and $R^4$ is substituted or unsubstituted $C_1$-$C_8$ alkyl.

The term "alkyl", as used herein, refers to saturated, monovalent or divalent hydrocarbon moieties having linear or branched moieties or combinations thereof and containing 1 to 8 carbon atoms. One methylene (—$CH_2$—) group, of the alkyl group can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can have one or more chiral centers. Alkyl groups can be independently substituted by halogen atoms, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups, ester groups, ketone groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen atoms, sulfonyl $C_{1-8}$ alkyl groups, sulfoxide $C_{1-8}$ alkyl groups, sulfonamide groups, nitro groups, cyano groups, $—OC_{1-8}$ alkyl groups, $—SC_{1-8}$ alkyl groups, $—C_{1-8}$ alkyl groups, $—C_{2-6}$ alkenyl groups, $—C_{2-6}$ alkynyl groups, ketone groups, alkylamino groups, amino groups, aryl groups, $C_{3-8}$ cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen atoms, sulfonyl groups, sulfoxide groups, nitro groups, cyano groups, $—OC_{1-6}$ alkyl groups, $—SC_{1-6}$ alkyl groups, $—C_{1-6}$ alkyl groups, $—C_{2-6}$ alkenyl groups, $—C_{2-6}$ alkynyl groups, ketone groups, alkylamino groups, amino groups, aryl groups, $C_{3-8}$ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. One methylene ($—CH_2—$) group, of the alkenyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. $C_{2-6}$ alkenyl can be in the E or Z configuration. Alkenyl groups can be substituted by alkyl groups, as defined above or by halogen atoms.

The term "alkynyl", as used herein, refers to a monovalent or divalent hydrocarbon radical having 2 to 6 carbon atoms, derived from a saturated alkyl, having at least one triple bond. One methylene ($—CH_2—$) group, of the alkynyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkynyl groups can be substituted by alkyl groups, as defined above, or by halogen atoms.

The term "heterocycle" as used herein, refers to a 3 to 10 membered ring, which can be aromatic or non-aromatic, saturated or unsaturated, containing at least one heteroatom selected form oxygen, nitrogen, sulfur, or combinations of at least two thereof, interrupting the carbocyclic ring structure. The heterocyclic ring can be interrupted by a C═O; the S and N heteroatoms can be oxidized. Heterocycles can be monocyclic or polycyclic. Heterocyclic ring moieties can be substituted by halogen atoms, sulfonyl groups, sulfoxide groups, nitro groups, cyano groups, $—OC_{1-6}$ alkyl groups, $—SC_{1-6}$ alkyl groups, $—C_{1-8}$ alkyl groups, $—C_{2-6}$ alkenyl groups, $—C_{2-6}$ alkynyl groups, ketone groups, alkylamino groups, amide groups, amino groups, aryl groups, $C_{3-8}$ cycloalkyl groups or hydroxyl groups. Examples of heterocycles are thiophene, benzothiophene, furan, benzofuran, indole.

The term "aryl" as used herein, refers to an organic moiety derived from an aromatic hydrocarbon consisting of a ring containing 6 to 10 carbon atoms, by removal of one hydrogen atom. Aryl can be substituted by halogen atoms, sulfonyl $C_{1-6}$ alkyl groups, sulfoxide $C_{1-6}$ alkyl groups, sulfonamide groups, carboxcyclic acid groups, $C_{1-6}$ alkyl carboxylates (ester) groups, amide groups, nitro groups, cyano groups, $—OC_{1-6}$ alkyl groups, $—SC_{1-6}$ alkyl groups, $—O_{1-6}$ alkyl groups, $—O_{2-6}$ alkenyl groups, $—C_{2-6}$ alkynyl groups, ketone groups, aldehydes, alkylamino groups, amino groups, aryl groups, $C_{3-8}$ cycloalkyl groups or hydroxyl groups. Aryls can be monocyclic or polycyclic.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as $—C(O)R^x$ wherein $R^x$ can be alkyl, aryl, cycloalkyl, cycloalkenyl, heterocycle as defined above.

The term "ester" as used herein, represents an organic compound having a carbonyl group linked to a carbon atom such as $—C(O)OR^x$ wherein $R^x$ can be alkyl, aryl, cycloalkyl, cycloalkenyl, heterocycle as defined above.

The term "amine" as used herein, represents a group of formula "$—NR^xR^y$", wherein $R^x$ and $R^y$ can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "$—SO_2^-$".

The term "sulfate" as used herein, represents a group of formula "$—O—S(O)_2—O—$".

The term "sulfonate" as used herein, represents a group of the formula "$—S(O)_2—O—$".

The term "carboxylic acid" as used herein, represents a group of formula "—C(O)ON".

The term "nitro" as used herein, represents a group of formula "$—NO_2$".

The term "cyano" as used herein, represents a group of formula "—CN".

The term "amide" as used herein, represents a group of formula "$—C(O)NR^xR^y$," or "$NR^xR^yC(O)—$," wherein $R^x$ and $R^y$ can be the same or independently H, alkyl, aryl, cycloalkyl, cycloalkenyl, heterocycle as defined above.

The term "sulfonamide" as used herein, represents a group of formula "$—S(O)_2NR^xR^y$" wherein $R^x$ and $R^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "$—P(O)(OH)_2$".

The term "phosphoric acid" as used herein, represents a group of formula "$—OP(O)(OH)_2$".

The term "sulphonic acid" as used herein, represents a group of formula "$—S(O)_2OH$".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Other defined terms are used throughout this specification:

"DCE" refers to dichloroethane

"DCM" refers to dichloromethane

"DMF" refers to dimethylformamide

"EDC" refers to 1-ethyl-3-(3-dimethylaminopropyl)carbodiimide

"PDGF" refers to platelet derived growth factor

"PTKs" refers to protein tyrosine kinase

"RTKs" refers to receptor tyrosine kinase

"THF" refers to tetrahydrofuran

"VEGF" refers to vascular endothelial growth factor

"VEGFR" refers to vascular endothelial growth factor receptor

Compounds of the invention are:

1-[4-chloro-3-(trifluoromethyl)phenyl]-3-{2-[5-(2H-tetrazol-5-yl)pyridin-3-yl]-1-benzothien-5-yl}urea;

1-{2-[2-amino-5-(2H-tetrazol-5-yl)pyridin-3-yl]-1-benzothien-5-yl}-3-[4-chloro-3-(trifluoromethyl)phenyl]urea;

1-(2-{2-amino-5-[2-(3-hydroxypropyl)-2H-tetrazol-5-yl]pyridin-3-yl}-1-benzothien-5-yl)-3-[4-chloro-3-(trifluoromethyl)phenyl]urea;

1-(2-{2-amino-5-[2-(3-hydroxypropyl)-2H-tetrazol-5-yl]pyridin-3-yl}-1-benzothien-5-yl)-3-[4-fluoro-3-(trifluoromethyl)phenyl]urea;

1-(2-{2-amino-5-[2-(3-hydroxypropyl)-2H-tetrazol-5-yl]pyridin-3-yl}-1-benzothien-5-yl)-3-[3-fluoro-5-(trifluoromethyl)phenyl]urea;

1-(2-{2-amino-5-[2-(3-hydroxypropyl)-2H-tetrazol-5-yl]pyridin-3-yl}-1-benzothien-5-yl)-3-[3,5-bis(trifluoromethyl)phenyl]urea;

1-(2-{2-amino-5-[1-(3-hydroxypropyl)-1H-tetrazol-5-yl]pyridin-3-yl}-1-benzothien-5-yl)-3-[4-chloro-3-(trifluoromethyl)phenyl]urea;

1-(2-{2-amino-5-[2-(2-hydroxyethyl)-2H-tetrazol-5-yl]pyridin-3-yl}-1-benzothien-5-yl)-3-[4-chloro-3-(trifluoromethyl)phenyl]urea;

N-[3-({5-[2-(3-hydroxypropyl)-2H-tetrazol-5-yl]pyridin-3-yl}ethynyl)phenyl]-3-methyl-2-furamide;

N-[3-({5-[2-(3-hydroxypropyl)-2H-tetrazol-5-yl]pyridin-3-yl}ethynyl)phenyl]-3-methylbenzamide;

1-[3-({2-amino-5-[2-(3-hydroxypropyl)-2H-tetrazol-5-yl]pyridin-3-yl}ethynyl)phenyl]-3-[4-chloro-3-(trifluoromethyl)phenyl]urea;

1-[2-fluoro-5-(trifluoromethyl)phenyl]-3-[4-({5-[2-(3-hydroxypropyl)-2H-tetrazol-5-yl]pyridin-3-yl}ethynyl)phenyl]urea;

1-[2-(2-amino-5-pyrimidin-2-ylpyridin-3-yl)-1-benzothien-5-yl]-3-[4-chloro-3-(trifluoromethyl)phenyl]urea;

1-[2-(2-amino-5-pyrazin-2-ylpyridin-3-yl)-1-benzothien-5-yl]-3-[4-chloro-3-(trifluoromethyl)phenyl]urea.

Compounds of formula I are useful as protein kinase inhibitors. As such, compounds of formula I will be useful for treating diseases related to unregulated protein kinase signal transduction, for example, cancer, blood vessel proliferative disorders, fibrotic disorders, inflammatory disorders and neurodegenerative diseases. In particular, the compounds of the present invention are useful for treatment of mesangial cell proliferative disorders and metabolic diseases, lung carcinomas, breast carcinomas, Non Hodgkin's lymphomas, ovarian carcinoma, pancreatic cancer, malignant pleural mesothelioma, melanoma, arthritis, restenosis, hepatic cirrhosis, atherosclerosis, psoriasis, rosacea, diabetic mellitus, wound healing, inflammation and neurodegenerative diseases and preferably ophthalmic diseases, i.e. diabetic retinopathy, retinopathy of prematurity, macular edema, retinal vein occlusion, exudative or neovascular age-related macular degeneration, high-risk eyes (i.e. fellow eyes have neovascular age-related macular degeneration) with dry age-related macular degeneration, neovascular disease associated with retinal vein occlusion, neovascular disease (including choroidal neovascularization) associated with the following: pathologic myopia, pseudoxanthoma elasticum, optic nerve drusen, traumatic choroidal rupture, atrophic macular degeneration, geographic atrophy, central serous retinopathy, cystoid macular edema, diabetic retinopathy, proliferative diabetic retinopathy, diabetic macular edema, rubeosis iridis, retinopathy of prematurity, Central and branch retinal vein occlusions, inflammatory/infectious retinal, neovascularization/edema, corneal neovascularization, hyperemia related to an actively inflamed pterygia, recurrent pterygia following excisional surgery, post-excision, progressive pterygia approaching the visual axis, prophylactic therapy to prevent recurrent pterygia, of post-excision, progressive pterygia approaching the visual axis, chronic low grade hyperemia associated with pterygia, neovascular glaucoma, iris neovascularization, idiopathic etiologies, presumed ocular histoplasmosis syndrome, retinopathy of prematurity, chronic allergic conjunctivitis, ocular rosacea, blepharoconjunctivitis, recurrent episcleritis, keratoconjunctivitis sicca, ocular graft vs host disease, etc.

Some compounds of Formula I and some of their intermediates may have at least one asymmetric center in their structure. This asymmetric center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahl & Camille G. Wermuth (Eds), Verlag Helvetica Chimica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.0001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene. Other excipient components which may be included in the ophthalmic preparations are chelating agents. The preferred chelating agent is edentate disodium, although other chelating agents may also be used in place of or in conjunction with it.

The ingredients are usually used in the following amounts:

Ingredient Amount (% w/v)
active ingredient about 0.001-5
preservative 0-0.10
vehicle 0-40
tonicity adjustor 0-10
buffer 0.01-10
pH adjustor q.s. pH 4.5-7.8
antioxidant as needed
surfactant as needed
purified water to make 100%

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 μl.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The present invention is further directed to pharmaceutical compositions comprising a pharmaceutically effective amount of one or more of the above-described compounds and a pharmaceutically acceptable carrier or excipient, wherein said compositions are effective for treating the above diseases and conditions; especially ophthalmic diseases and conditions. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, rosacea, atherosclerosis, arthritis, and other disorders related to abnormal vasculogenesis and/or angiogenesis, such as exudative age related macular degeneration and diabetic retinopathy.

The present invention is further directed to pharmaceutical compositions comprising a pharmaceutically effective amount of the above-described compounds and a pharmaceutically acceptable carrier or excipient. Such a composition is believed to modulate signal transduction by a protein kinase, tyrosine kinase, either by inhibition of catalytic activity, affinity to ATP or ability to interact with a substrate.

The present invention relates to compounds capable of regulating and/or modulating tyrosine kinase signal transduction and more particularly receptor and non-receptor tyrosine kinase signal transduction.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences,* $18^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered orally, subcutaneously, intravenously, intrathecally or some suitable combination(s) thereof.

In addition to the common dosage forms set out above, the compounds of this invention may also be administered by controlled release means and/or delivery devices such as those described in U.S. Pat. Nos. 3,845,770; 3,916,899; 3,536,809; 3,598,123; 3,630,200; 4,008,719; and 5,366,738.

For use where a composition for intravenous administration is employed, a suitable daily dosage range for anti-inflammatory, anti-atherosclerotic or anti-allergic use is from about 0.001 mg to about 25 mg (preferably from 0.01 mg to about 1 mg) of a compound of this invention per kg of body weight per day and for cytoprotective use from about 0.1 mg to about 100 mg (preferably from about 1 mg to about 100 mg and more preferably from about 1 mg to about 10 mg) of a compound of this invention per kg of body weight per day. For the treatment of diseases of the eye, ophthalmic preparations for ocular administration comprising 0.001-1% by weight solutions or suspensions of the compounds of this invention in an acceptable ophthalmic formulation may be used.

Preferably, the pharmaceutical preparation is in a unit dosage form. In such form, the preparation is subdivided into suitably sized unit doses containing appropriate quantities of the active component, e.g., an effective amount to achieve the desired purpose.

The magnitude of prophylactic or therapeutic dose of a compound of this invention will, of course, vary with the nature of the severity of the condition to be treated and with the particular compound and its route of administration. It will also vary according to the age, weight and response of the individual patient. It is understood that a specific daily dosage amount can simultaneously be both a therapeutically effective amount, e.g., for treatment to slow progression of an existing condition, and a prophylactically effective amount, e.g., for prevention of condition.

The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the compounds of the present invention. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

In one aspect, the present invention provides a kit comprising a therapeutically effective amount of at least one compound of the present invention, or a pharmaceutically acceptable salt of said compound and a pharmaceutically acceptable carrier, vehicle or diluents, and directions for the use of said kit.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/ or the non-receptor tyrosine kinases and interfering with the signal transduced by such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

The present invention concerns also processes for preparing the compounds of Formula I. The compounds of formula I according to the invention can be prepared analogously to conventional methods as understood by the person skilled in the art of synthetic organic chemistry. Synthetic Schemes set forth below, illustrate how the compounds according to the invention can be made.

Scheme 1

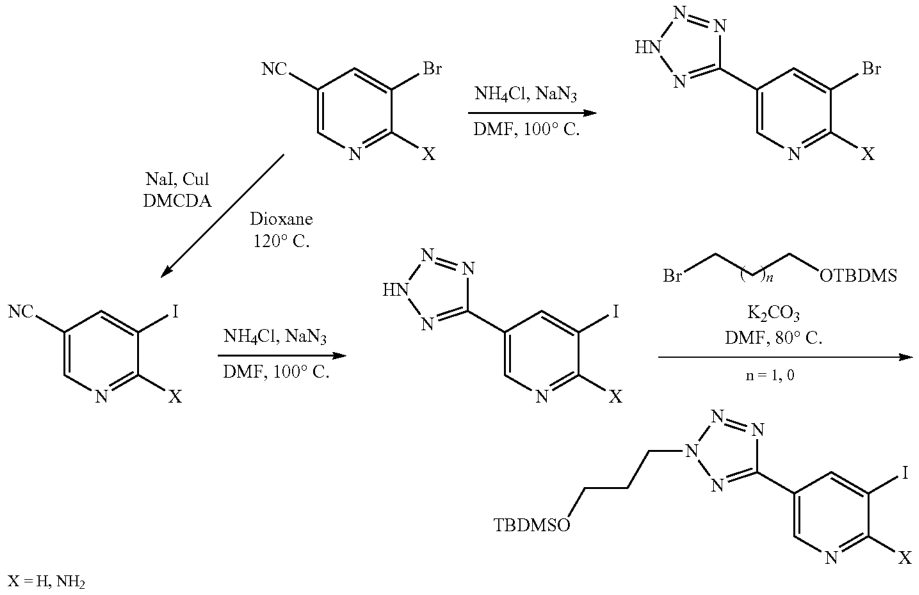

Scheme 2

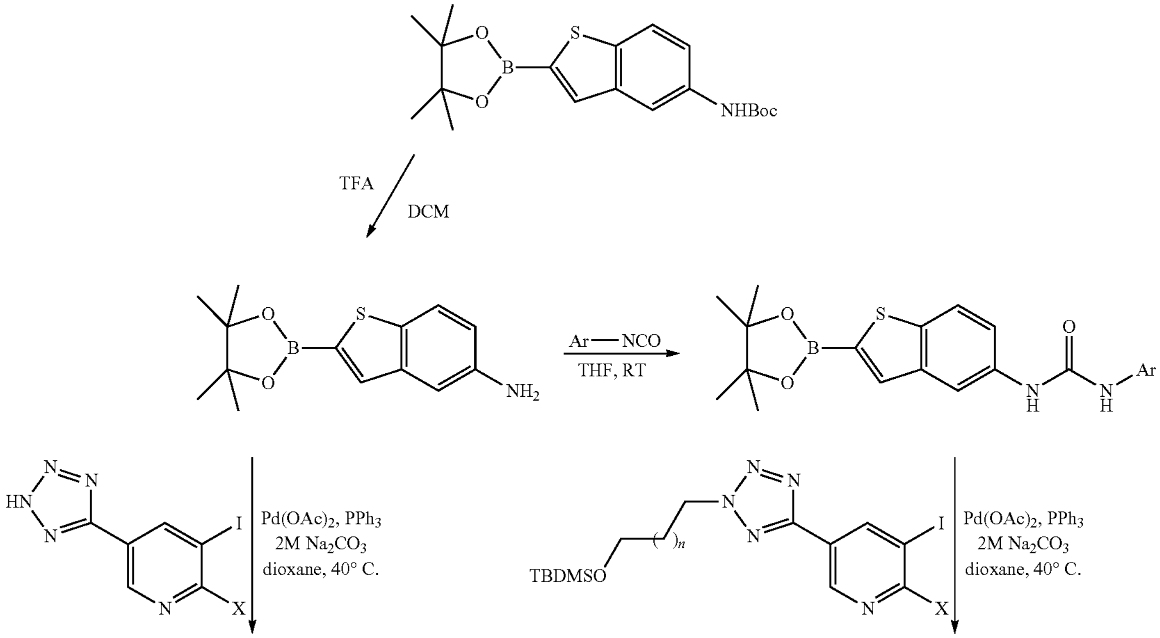

-continued
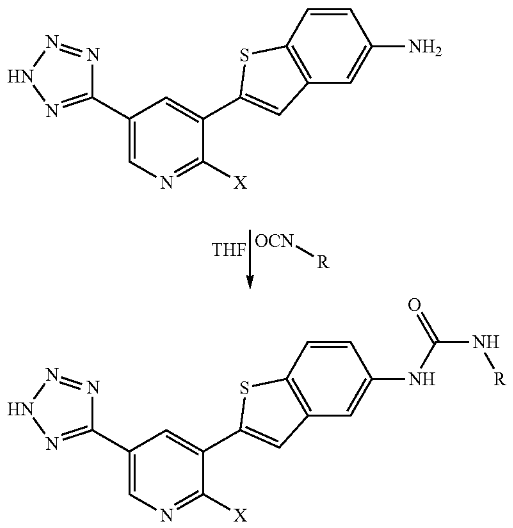
X = H, $NH_2$
n = 0, 1
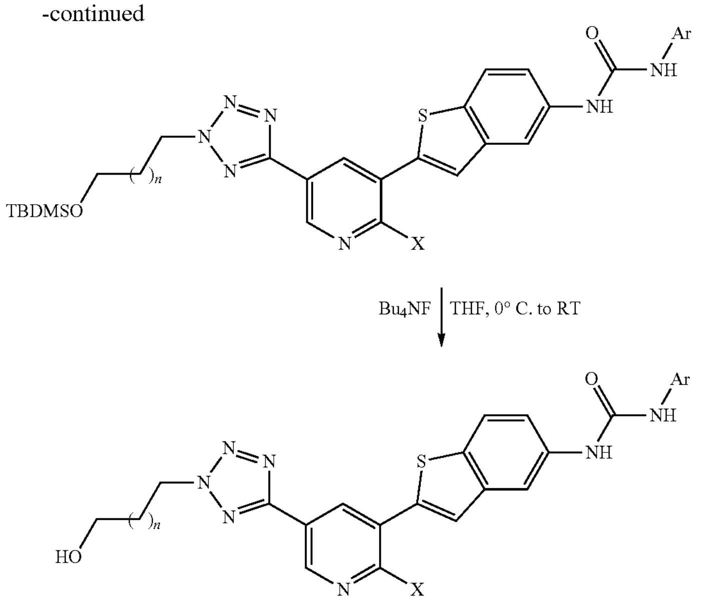
Scheme 3
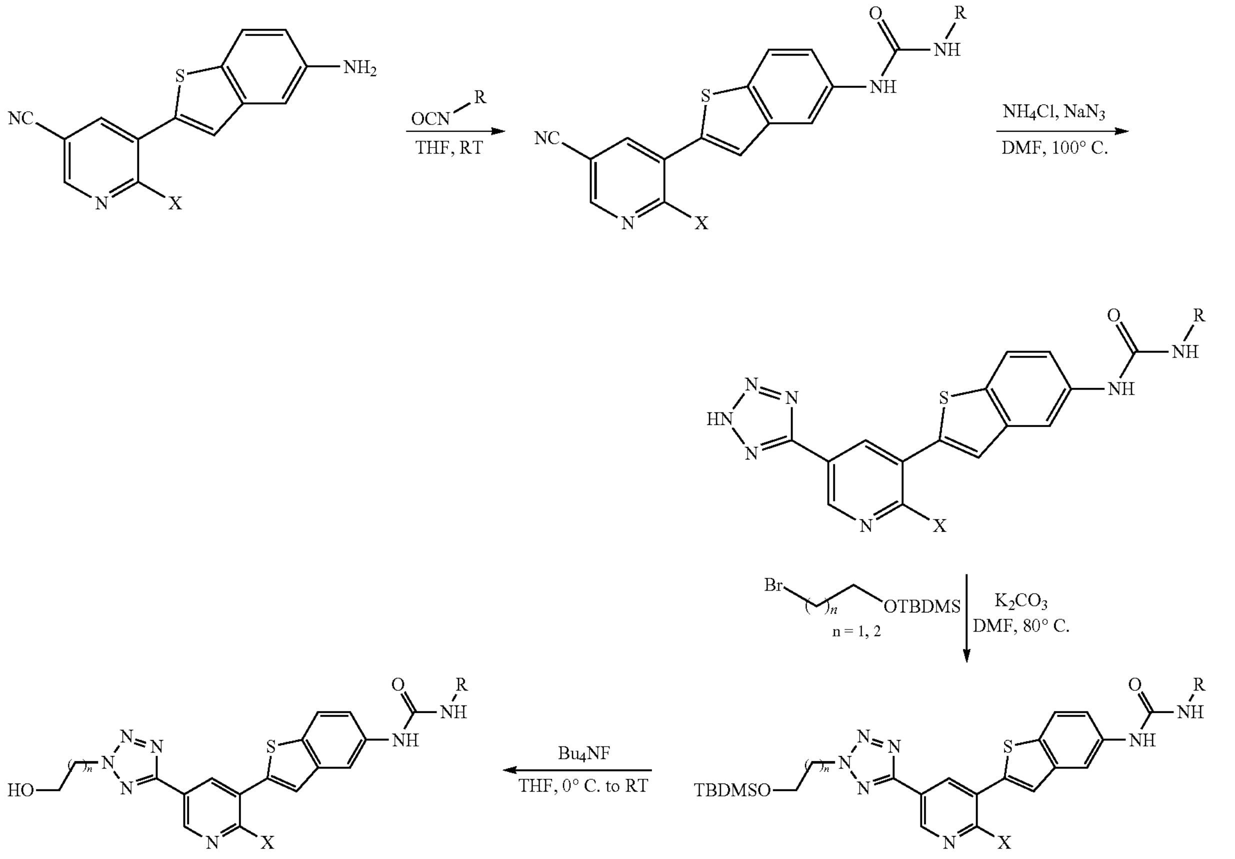
X = H, $NH_2$ Scheme 4
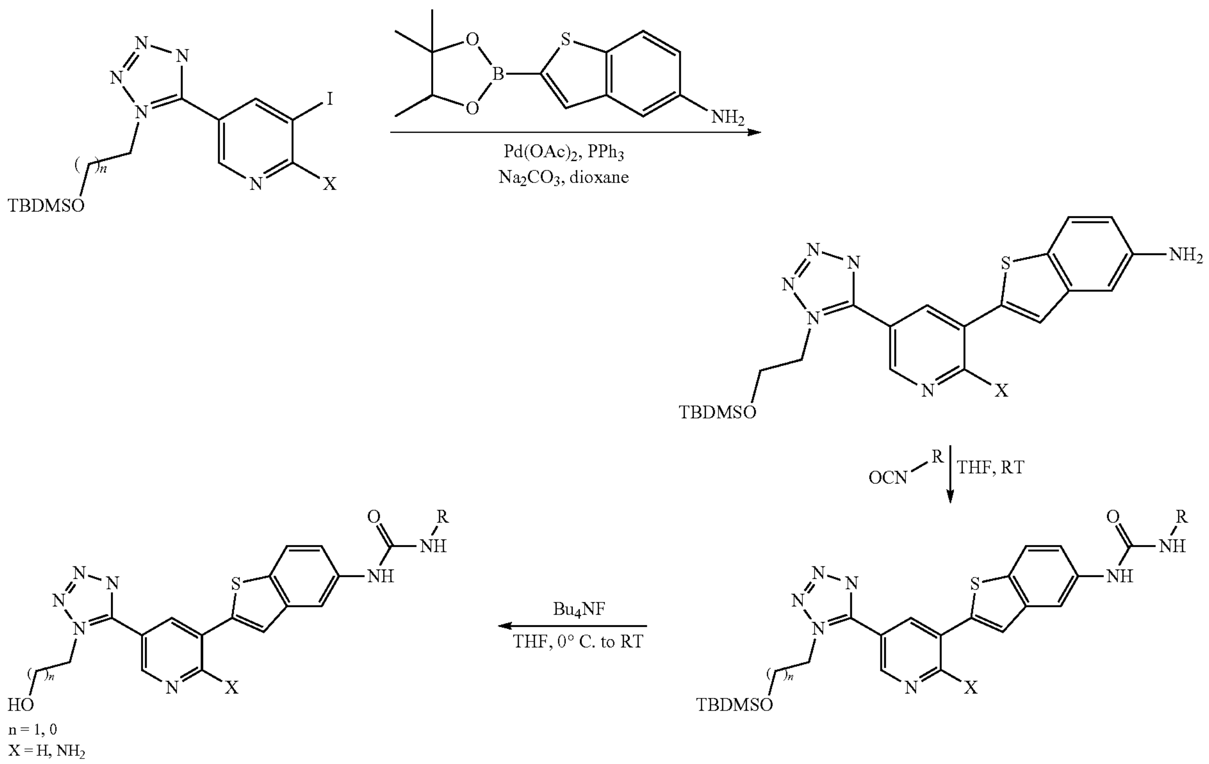
Scheme 5
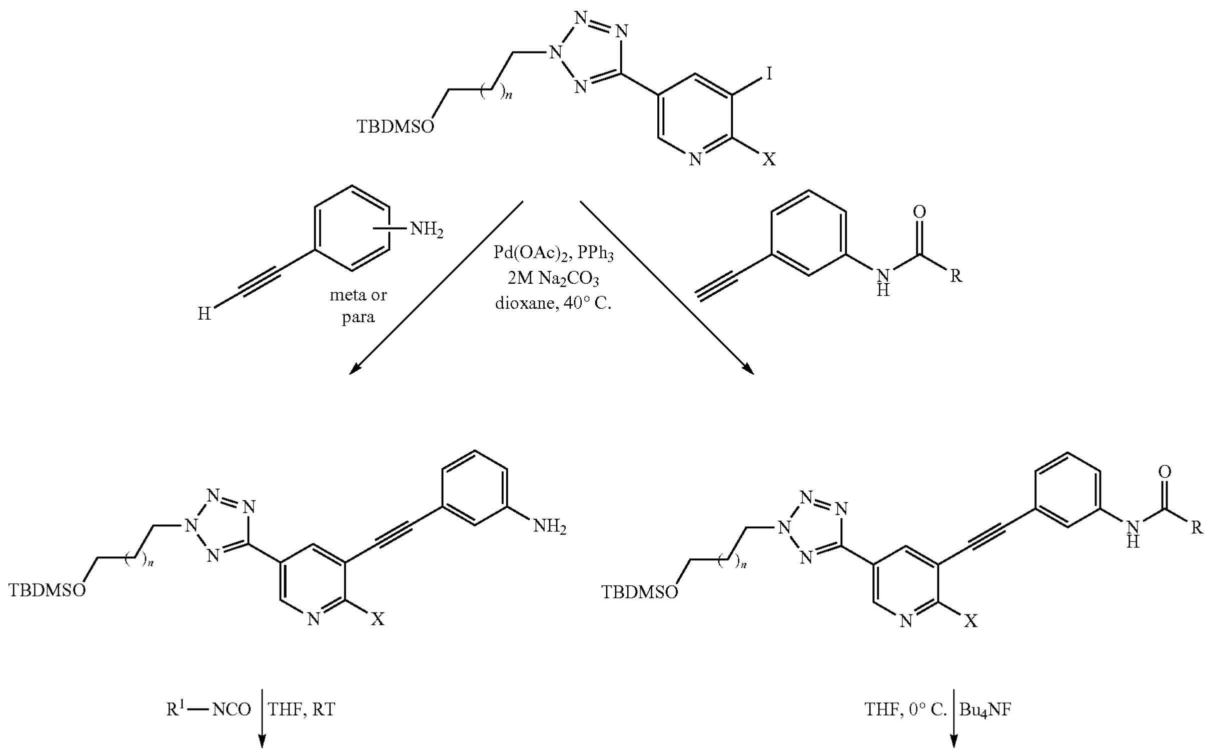

-continued

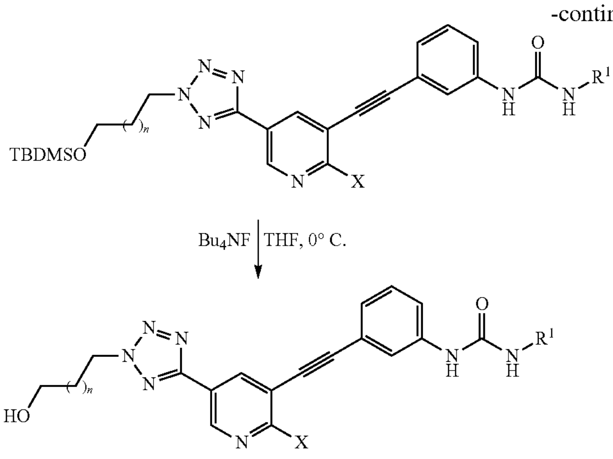

X = H, $NH_2$
n = 0, 1

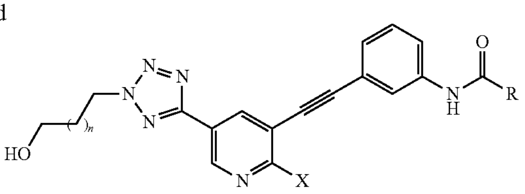

At this stage, those skilled in the art will appreciate that many additional compounds that fall under the scope of the invention may be prepared by performing various common chemical reactions. Details of certain specific chemical transformations are provided in the examples.

Those skilled in the art will be able to routinely modify and/or adapt the following scheme to synthesize any compounds of the invention covered by Formula I. The present invention is not to be limited in scope by the exemplified embodiments which are intended as illustrations of single aspects of the invention only. Indeed, various modifications of the invention in addition to those described herein will become apparent to those skilled in the art from the foregoing description.

DETAILED DESCRIPTION OF THE INVENTION

The present invention relates to organic molecules capable of modulating, regulating and/or inhibiting protein kinase signal transduction, useful for treating diseases related to protein kinase signal transduction, for example, cancer, blood vessel proliferative disorders, fibrotic disorders, and neurodegenerative diseases. In particular, the compounds of the present invention are useful for treatment of mesangial cell proliferative disorders and metabolic diseases, lung carcinomas, breast carcinomas, Non Hodgkin's lymphomas, ovarian carcinoma, pancreatic cancer, malignant pleural mesothelioma, melanoma, arthritis, restenosis, hepatic cirrhosis, atherosclerosis, psoriasis, rosacea, diabetic mellitus, wound healing, inflammation and neurodegenerative diseases and preferably ophthalmic diseases, i.e. diabetic retinopathy, retinopathy of prematurity, macular edema, retinal vein occlusion, exudative or neovascular age-related macular degeneration, high-risk eyes (i.e. fellow eyes have neovascular age-related macular degeneration) with dry age-related macular degeneration, neovascular disease associated with retinal vein occlusion, neovascular disease (including choroidal neovascularization) associated with the following: pathologic myopia, pseudoxanthoma elasticum, optic nerve drusen, traumatic choroidal rupture, atrophic macular degeneration, geographic atrophy, central serous retinopathy, cystoid macular edema, diabetic retinopathy, proliferative diabetic retinopathy, diabetic macular edema, rubeosis iridis, retinopathy of prematurity, Central and branch retinal vein occlusions, inflammatory/infectious retinal, neovascularization/edema, corneal neovascularization, hyperemia related to an actively inflamed pterygia, recurrent pterygia following excisional surgery, post-excision, progressive pterygia approaching the visual axis, prophylactic therapy to prevent recurrent pterygia, of post-excision, progressive pterygia approaching the visual axis, chronic low grade hyperemia associated with pterygia, neovascular glaucoma, iris neovascularization, idiopathic etiologies, presumed ocular histoplasmosis syndrome, retinopathy of prematurity, chronic allergic conjunctivitis, ocular rosacea, blepharoconjunctivitis, recurrent episcleritis, keratoconjunctivitis sicca, ocular graft vs host disease, etc.

In another aspect, the invention provides the use of at least one kinase inhibitor for the manufacture of a medicament for the treatment of a disease or a condition mediated by tyrosine kinases in a mammal.

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^{2}H$ (or D) in place of hydrogen $^{1}H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with ACDLabs version 12.5. Some of the intermediate and reagent names used in the examples were generated with software such as Chem Bio Draw Ultra version 12.0 or Auto Nom 2000 from MDL ISIS Draw 2.5 SP1.

In general, characterization of the compounds is performed according to the following methods; NMR spectra are recorded on 300 or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by medium pressure liquid chromatography, unless noted otherwise.

Examples

Intermediate 1

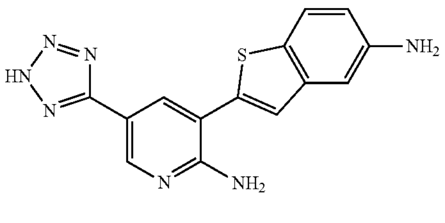 [SMILES: Nc1ccc2sc(-c3cc(-c4nn[nH]n4)cnc3N)cc2c1]

3-(5-amino-1-benzothien-2-yl)-5-(2H-tetrazol-5-yl)pyridin-2-amine

The reaction mixture of 3-iodo-5-(2H-tetrazol-5-yl)pyridin-2-amine (288 mg, 1.0 mmol, 1 eq), 2-(4,4,5,5-tetramethyl-1,3,2-dioxaborolan-2-yl)benzo[b]thiophen-5-amine (330 mg, 1.2 eq), triphenylphosphine (53 mg, 0.2 eq), and palladium diacetate (22 mg, 0.1 eq) in dioxane (3 mL) and aqueous sodium carbonate (2 M, 2 mL, 4 eq) under nitrogen atmosphere was vigorously stirred and heated at 40° C. for 30 minutes. The mixture was then partitioned between aqueous ammonium chloride and THF-EtOAc (1:10). The organic layer was isolated and dried with anhydrous sodium sulfate. The upper solution was concentrated down with silica gel. Upon a gradient column chromatography (EtOAc to MeOH-EtOAc 1:10) 3-(5-amino-1-benzothien-2-yl)-5-(2H-tetrazol-5-yl)pyridin-2-amine was obtained in the amount of 5 mg.

$^1$H NMR (600 MHz, DMSO-$d_6$) δ ppm 8.57 (d, J=1.76 Hz, 1H) 8.07 (d, J=1.76 Hz, 1H) 7.59 (d, J=8.51 Hz, 1H) 7.43 (s, 1H) 6.98 (d, J=1.76 Hz, 1H) 6.73 (dd, J=8.51, 1.91 Hz, 1H) 6.06 (br. s., 2H) 5.11 (br. s., 2H).

Compound 1

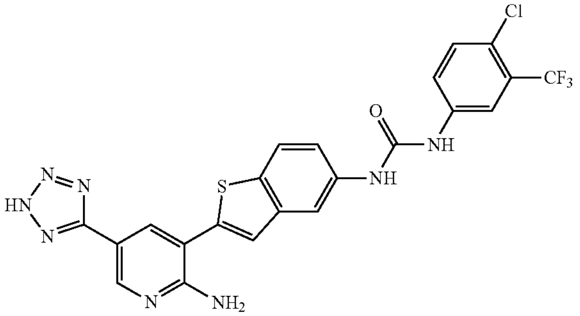 [SMILES: Nc1ncc(-c2nn[nH]n2)cc1-c1cc2cc(NC(=O)Nc3ccc(Cl)c(C(F)(F)F)c3)ccc2s1]

1-[4-chloro-3-(trifluoromethyl)phenyl]-3-{2-[5-(2H-tetrazol-5-yl)pyridin-3-yl]-1-benzothien-5-yl}urea To the solution of 5-bromo-3-cyanopyridine (3.0 g, 15.9 mmol, 1 eq) in anhydrous dimethylformamide (40 mL) was added ammonium chloride (1.45 g, 1.7 eq) and sodium azide (1.76 g, 1.7 eq). The resulting reaction mixture was heated at 100° C. under nitrogen for 20 hours. After the reaction mixture was cooled to room temperature, it was poured into ice-water and the pH of the mixture was adjusted to ~3.5 using aqueous hydrochloric acid (2 N). The aqueous was first extracted with ethyl acetate three times, followed by an extraction with i-PrOH—$CHCl_3$ (1:4). All organics were combined and dried with anhydrous sodium sulfate. The upper clear liquor was decanted, concentrated under reduced pressure, and the resulting oily residue was placed under high vacuum for 20 hours. Upon treatment with EtOAc-Hex (1:1) and filtration, 3-bromo-5-(2H-tetrazol-5-yl)pyridine was obtained as a white solid in the amount of 3.241 g.

$^1$H NMR (600 MHz, DMSO-$d_6$) δ ppm 9.19 (d, J=1.76 Hz, 1H) 8.92 (d, J=2.20 Hz, 1H) 8.61 (t, J=2.05 Hz, 1H)

The reaction mixture of 3-bromo-5-(2H-tetrazol-5-yl)pyridine (226 mg, 1.0 mmol, 1 eq), 2-(4,4,5,5-tetramethyl-1,3,2-dioxaborolan-2-yl)benzo[b]thiophen-5-amine (316 mg, 1.15 eq), triphenylphosphine (53 mg, 0.2 eq), and palladium diacetate (22 mg, 0.1 eq) in dioxane (3 mL) and aqueous sodium carbonate (2 M, 2 mL, 4 eq) under nitrogen atmosphere was vigorously stirred and heated at 100° C. for three hours. It was then cooled to room temperature, filtered through a Buchner funnel, and rinsed with small amount of water and ethyl acetate. The filtrate was isolated and concentrated down with silica gel. Upon a gradient column chromatography (EtOAc to MeOH-EtOAc 1:4), 2-(5-(2H-tetrazol-5-yl)pyridin-3-yl)benzo[b]thiophen-5-amine was obtained as an orange colored solid in the amount of 92 mg while the starting material, 3-bromo-5-(2H-tetrazol-5-yl)pyridine was recovered in the amount of 90 mg.

$^1$H NMR (300 MHz, DMSO-$d_6$) δ ppm 9.08 (s, 1H) 8.87 (d, J=1.76 Hz, 1H) 8.48 (s, 1H) 7.80 (s, 1H) 7.62 (d, J=8.50 Hz, 1H) 7.01 (d, J=0.73 Hz, 1H) 6.75 (dd, J=7.98, 0.95 Hz, 1H) 5.16 (br. s., 2H)

The reaction mixture of 2-(5-(2H-tetrazol-5-yl)pyridin-3-yl)benzo[b]thiophen-5-amine (44.1 mg, 0.15 mmol, 1 eq) and 4-chloro-3-(trifluoromethyl)phenyl isocyanate (33.2 mg, 1 eq) in anhydrous tetrahydrofuran (1.5 mL) under nitrogen atmosphere was stirred at room temperature for 45 minutes. The reaction was then diluted with ethyl acetate, washed with aqueous ammonium chloride, brine, and dried with anhydrous sodium sulfate. The upper clear solution was decanted and concentrated. The soft solid was wrapped with silica gel and chromatographed (EtOAc to MeOH-EtOAc 1:4) to give 1-[4-chloro-3-(trifluoromethyl)phenyl]-3-{2-[5-(2H-tetrazol-5-yl)pyridin-3-yl]-1-benzothien-5-yl}urea as a yellow powder in the amount of 26 mg.

$^1$H NMR (600 MHz, DMSO-$d_6$) δ ppm 9.42 (br. s., 1H) 9.20 (br. s., 1H) 9.12 (d, J=1.91 Hz, 1H) 8.93 (d, J=2.35 Hz, 1H) 8.53 (t, J=2.13 Hz, 1H) 8.16 (d, J=2.49 Hz, 1H) 8.13 (d, J=2.05 Hz, 1H) 8.04 (s, 1H) 7.94 (d, J=8.66 Hz, 1H) 7.68 (dd, J=8.73, 2.42 Hz, 1H) 7.61-7.64 (m, 1H) 7.44 (dd, J=8.80, 2.05 Hz, 1H).

Compound 2

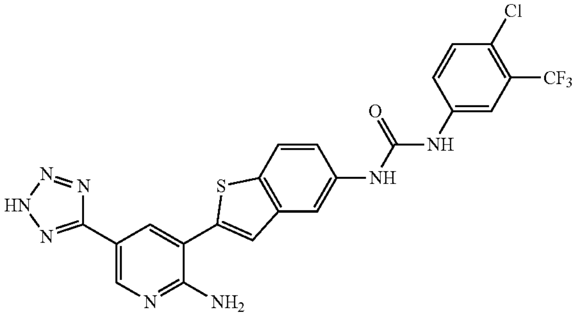 [SMILES: Nc1ncc(-c2nn[nH]n2)cc1-c1cc2cc(NC(=O)Nc3ccc(Cl)c(C(F)(F)F)c3)ccc2s1]

1-{2-[2-amino-5-(2H-tetrazol-5-yl)pyridin-3-yl]-1-benzothien-5-yl}-3-[4-chloro-3-(trifluoromethyl)phenyl]urea To the stirring mixture of 3-(5-aminobenzo[b]thiophen-2-yl)-5-isocyanopyridin-2-amine (1.064 g, 4 mmol, 1 eq) in anhydrous tetrahydrofuran (25 mL) under nitrogen atmosphere was added 4-chloro-3-(trifluoromethyl)phenyl isocyanate (904 mg, 1 eq) and the reaction mixture was stirred at room temperature for three hours. The reaction was then diluted with ethyl acetate, washed sequentially with aqueous ammonium chloride, saturated aqueous sodium bicarbonate, and brine, and dried with anhydrous sodium sulfate. The upper clear solution was decanted and concentrated under reduced pressure to lesser amount, to which was added a small amount of EtOAc-Hex (2:1). Upon a filtration, 1-(2-(2-amino-5-isocyanopyridin-3-yl)benzo[b]thiophen-5-yl)-3-(4-chloro-3-(trifluoromethyl)phenyl)urea was obtained as white solid in the amount of 1.37 g.

$^1$H NMR (600 MHz, DMSO-$d_6$) δ ppm 9.23 (s, 1H) 9.03 (s, 1H) 8.42 (d, J=2.05 Hz, 1H) 8.16 (d, J=2.05 Hz, 1H) 8.13 (d, J=1.76 Hz, 1H) 7.89-7.92 (m, 2H) 7.64-7.67 (m, 1H) 7.60-7.64 (m, 2H) 7.40 (dd, J=8.80, 1.76 Hz, 1H) 7.15 (br. s., 2H).

The mixture of 1-(2-(2-amino-5-isocyanopyridin-3-yl)benzo[b]thiophen-5-yl)-3-(4-chloro-3-(trifluoromethyl)phenyl)urea (1.3 g, 2.67 mmol, 1 eq), ammonium chloride (286 mg, 2 eq), and sodium azide (347 mg, 2 eq) in anhydrous dimethylformamide (8 mL) under nitrogen atmosphere was stirred and heated at 120° C. for 2 hours. The mixture was then cooled to room temperature and additional ammonium chloride (286 mg, 2 eq) and sodium azide (347 mg, 2 eq) were added. The reaction mixture was heated back to 120° C. and stirred at that temperature for another hour. After it was cooled to room temperature, it was transferred into a mixture of ethyl acetate and aqueous ammonium chloride; during the process, the pH of the aqueous layer was adjusted to 3~4ish by using aq $KHSO_4$ (10%). The organic layer was isolated, washed once with saturated brine, and dried with anhydrous sodium sulfate. The upper solution was decanted and concentrated down with silica gel. Upon gradient column chromatography (from EtOAc to MeOH-EtOAc 1:2), 1-{2-[2-amino-5-(2H-tetrazol-5-yl)pyridin-3-yl]-1-benzothien-5-yl}-3-[4-chloro-3-(trifluoromethyl)phenyl]urea was obtained as a yellow solid in the amount of 452 mg.

$^1$H NMR (600 MHz, DMSO-$d_6$) δ ppm 9.29 (s, 1H) 9.07 (s, 1H) 8.61 (s, 1H) 8.16 (br. s., 1H) 8.11 (br. s., 2H) 7.91 (d, J=8.51 Hz, 1H) 7.65-7.69 (m, 2H) 7.61-7.64 (m, 1H) 7.41 (d, J=8.22 Hz, 1H) 6.28 (br. s., 2H).

Intermediate 2

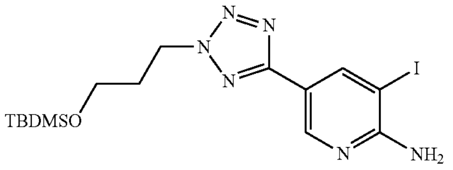 [SMILES: CC(C)(C)[Si](C)(C)OCCCn1nnc(-c2cnc(N)c(I)c2)n1]

5-(2-(3-((tert-butyldimethylsilyl)oxy)propyl)-2H-tetrazol-5-yl)-3-iodopyridin-2-amine The mixture of 6-amino-5-bromonicotinonitrile (3.315 g, 15.9 mmol, 1 eq), sodium iodide (4.77 g, 2 eq), copper(I) iodide (303 mg, 0.1 eq), and trans-N,N'-dimethylcyclohexane-1,2-diamine (0.52 mL, 0.2 eq) in anhydrous dioxane (40 mL under nitrogen atmosphere was stirred at 120° C. for 20 hours. The mixture was cooled to room temperature then partitioned between ethyl acetate and aqueous ammonium chloride. The organic layer was isolated, further washed with saturated aqueous sodium bicarbonate, brine, and dried with anhydrous sodium sulfate. The upper solution was decanted, concentrated, and the crude solid residue was subject to a column chromatography started first with EtOAc-Hex (1:5 to 1:1) followed by MeOH—CHCl3 (1:100 to 1:20). Product containing fractions were all collected and concentrated. The solid residue was triturated with EtOAc-Hex (1:4) yielding 3-iodo-5-isocyanopyridin-2-amine as an off-white solid in the amount of 2.75 g upon filtration.

$^1$H NMR (600 MHz, DMSO-$d_6$) δ ppm 8.35 (d, J=1.76 Hz, 1H) 8.30 (d, J=1.76 Hz, 1H) 7.14 (br. s., 2H).

To the solution of 3-iodo-5-isocyanopyridin-2-amine (2.74 g, 11.2 mmol, 1 eq) in anhydrous dimethylformamide (25 mL) in a 100 mL round bottom flask was added ammonium chloride (1.02 g, 1.7 eq) and sodium azide (1.24 g, 1.7 eq). The resulting reaction mixture was heated to 100° C. under nitrogen for 20 hours. After the reaction mixture was cooled to room temperature, it was poured into ice-chunk filled water and the pH of the mixture was adjusted to ~3.5 using aqueous hydrochloric acid (2 N). After the mixture was stirred at room temperature for about two hours, it was filtered through a Buchner funnel, rinsed with water, giving a brown solid. The solid was treated with MeOH—$CHCl_3$ and concentrated down with silica gel. Upon gradient column chromatography (MeOH-EtOAc 1:20 to 1:5), 3-iodo-5-(2H-tetrazol-5-yl)pyridin-2-amine was obtained as off-white solid in the amount of 1.15 g.

$^1$H NMR (600 MHz, DMSO-d$_6$) δ ppm 8.60 (d, J=1.76 Hz, 1H) 8.45 (d, J=2.05 Hz, 1H) 6.77 (br. s., 2H).

The reaction mixture of 3-iodo-5-(2H-tetrazol-5-yl)pyridin-2-amine (0.61 g, 2.12 mmol, 1 eq), (3-bromopropoxy)-tert-butyldimethylsilane (0.66 mL, 1.3 eq), and potassium carbonate (0.44 g, 1.5 eq) in anhydrous dimethylformamide (8 mL) was stirred and heated at 80° C. under nitrogen atmosphere for 2 hours. It was then diluted with ethyl acetate, washed sequentially with aqueous ammonium chloride, saturated aqueous sodium bicarbonate, and brine, and dried with anhydrous sodium sulfate. The upper clear solution was decanted and concentrated under reduced pressure with silica gel. A gradient column chromatography [Hexane to EtOAc-Hex (1:2)] rendered 5-(2-(3-((tert-butyldimethylsilyl)oxy)propyl)-2H-tetrazol-5-yl)-3-iodopyridin-2-amine as a white solid in the amount of 797 mg.

$^1$H NMR (600 MHz, DMSO-d$_6$) δ ppm 8.60 (d, J=1.76 Hz, 1H) 8.40 (d, J=1.76 Hz, 1H) 6.63 (br. s., 2H) 4.74 (t, J=6.75 Hz, 2H) 3.63 (t, J=5.72 Hz, 2H) 2.14 (quin, J=6.24 Hz, 2H) 0.85 (s, 9H) 0.01 (s, 6H).

Compound 3

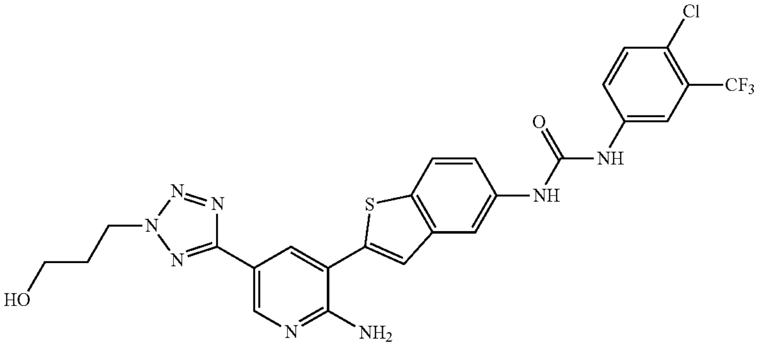 [SMILES: Nc1ncc(-c2nnn(CCCO)n2)cc1-c1cc2cc(NC(=O)Nc3ccc(Cl)c(C(F)(F)F)c3)ccc2s1]

1-(2-{2-amino-5-[2-(3-hydroxypropyl)-2H-tetrazol-5-yl]pyridin-3-yl}-1-benzothien-5-yl)-3-[4-chloro-3-(trifluoromethyl)phenyl]urea To the solution of tert-butyl (2-(4,4,5,5-tetramethyl-1,3,2-dioxaborolan-2-yl)benzo[b]thiophen-5-yl)carbamate (7.51 g, 20 mmol, 1 eq) in anhydrous dichloromethane (40 mL under nitrogen atmosphere at 0° C. was added dropwise trifluoroacetic acid (15.4 mL, 10 eq) and the reaction was stirred at 0° C. for 30 minutes followed by at room temperature for about two hours. The reaction was then slowly poured into an ice-cold saturated aqueous sodium bicarbonate solution with stirring and the white solid that appeared during the process was filtered, washed with water, to give a first batch of 2-(4,4,5,5-tetramethyl-1,3,2-dioxaborolan-2-yl)benzo[b]thiophen-5-amine in the amount of 2.792 g. The pH of the filtrate was adjusted to 8 by addition of solid sodium bicarbonate with stirring and then extracted using chloroform (3×). All organic layers were combined, dried with anhydrous sodium sulfate, and concentrated down to give brown oil. After the oil was placed in vacuo for two hours, it was treated with EtOAc-Hex (1:9) and the mixture was stirred at room temperature for 30 minutes. A second batch of 2-(4,4,5,5-tetramethyl-1,3,2-dioxaborolan-2-yl)benzo[b]thiophen-5-amine was isolated as a pale pink solid in the amount of 1.883 g upon filtration. The total amount of 2-(4,4,5,5-tetramethyl-1,3,2-dioxaborolan-2-yl)benzo[b]thiophen-5-amine is 4.675 g with a yield of 85%.

$^1$H NMR (600 MHz, DMSO-d$_6$) δ ppm 7.60-7.62 (m, 2H) 7.01 (d, J=2.05 Hz, 1H) 6.80 (dd, J=8.66, 2.20 Hz, 1H) 5.18 (br. s., 2H) 1.30 (s, 12H)

To the solution of 2-(4,4,5,5-tetramethyl-1,3,2-dioxaborolan-2-yl)benzo[b]thiophen-5-amine (825 mg, 3 mmol, 1 eq) in anhydrous tetrahydrofuran (15 mL) was added 4-chloro-3-(trifluoromethyl)phenyl isocyanate (678.3 mg, 1 eq) and the reaction solution was stirred at room temperature under nitrogen atmosphere overnight. The reaction was then diluted with ethyl acetate, washed sequentially with aqueous ammonium chloride, saturated aqueous sodium bicarbonate, and brine, and dried with anhydrous sodium sulfate. The upper clear solution was decanted and concentrated under reduced pressure. 1-(4-chloro-3-(trifluoromethyl)phenyl)-3-(2-(4,4,5,5-tetramethyl-1,3,2-dioxaborolan-2-yl)benzo[b]thiophen-5-yl)urea was obtained as slightly brown colored foam in vacuo in the amount of 1.5 g which was used directly without further purification.

$^1$H NMR (600 MHz, DMSO-d$_6$) δ ppm 9.18 (s, 1H) 8.99 (s, 1H) 8.15 (dd, J=10.12, 1.91 Hz, 2H) 7.92 (d, J=8.80 Hz, 1H) 7.85 (s, 1H) 7.64-7.66 (m, 1H) 7.61-7.63 (m, 1H) 7.44 (dd, J=8.80, 1.76 Hz, 1H) 1.33 (s, 12H).

To the mixture of 5-(2-(3-((tert-butyldimethylsilyl)oxy)propyl)-2H-tetrazol-5-yl)-3-iodopyridin-2-amine (184 mg, 0.4 mmol, 1 eq) and 1-(4-chloro-3-(trifluoromethyl)phenyl)-3-(2-(4,4,5,5-tetramethyl-1,3,2-dioxaborolan-2-yl)benzo[b]thiophen-5-yl)urea (218 mg, 1.1 eq) in dioxane (3 mL) and water (0.75 mL) under nitrogen atmosphere was added potassium acetate (157 mg, 4 eq) and [1,1'-bis(diphenylphosphino)ferocene]dichloropalladium(II) (complex with dichloromethane, 65 mg, 0.2 eq). After the mixture was stirred at 40° C. for 30 minutes, additional amount of (46 mg) and palladium catalyst (50 mg) were added and the reaction was continued at that temperature for an hour. The mixture was then diluted with ethyl acetate, washed sequentially with aqueous ammonium chloride, saturated aqueous sodium bicarbonate, and brine, and dried with anhydrous sodium sulfate. The upper clear solution was decanted and concentrated and loaded onto silica. Gradient column chromatography (EtOAc-Hex 1:4 to 6:1) gave a brown solid which was triturated with EtOAc-Hex (3:2) rendering 1-(2-(2-amino-5-

(2-(3-((tert-butyldimethylsilyl)oxy)propyl)-2H-tetrazol-5-yl)pyridin-3-yl)benzo[b]thiophen-5-yl)-3-(4-chloro-3-(trifluoromethyl)phenyl)urea as an off-white solid in the amount of 90 mg.

$^1$H NMR (600 MHz, DMSO-$d_6$) δ ppm 9.20 (s, 1H) 9.00 (s, 1H) 8.67 (d, J=2.05 Hz, 1H) 8.16 (d, J=2.05 Hz, 1H) 8.13 (d, J=1.76 Hz, 1H) 8.09 (d, J=2.05 Hz, 1H) 7.91 (d, J=8.51 Hz, 1H) 7.69 (s, 1H) 7.64-7.67 (m, 1H) 7.61-7.64 (m, 1H) 7.41 (dd, J=8.66, 1.91 Hz, 1H) 6.68 (s, 2H) 4.76 (t, J=6.75 Hz, 2H) 3.65 (t, J=5.72 Hz, 2H) 2.16 (quin, J=6.24 Hz, 2H) 0.85 (s, 9H) 0.02 (s, 6H).

To the solution of 1-(2-(2-amino-5-(2-(3-((tert-butyldimethylsilyl)oxy)propyl)-2H-tetrazol-5-yl)pyridin-3-yl)benzo[b]thiophen-5-yl)-3-(4-chloro-3-(trifluoromethyl)phenyl) urea (100 mg, 0.142 mmol, 1 eq) in anhydrous tetrahydrofuran (3 mL) under nitrogen atmosphere at 0° C. was added dropwise a solution of tetrabutylammonium fluoride (1.0 M in THF, 0.43 mL, 3 eq). The reaction was stirred at room temperature for 2 hours and then partitioned between ethyl acetate and aqueous ammonium chloride. The organic layer was isolated, further washed with saturated aqueous sodium bicarbonate, brine, and dried with anhydrous sodium sulfate. The upper clear solution was decanted and concentrated and loaded onto silica. The mixture was subject to a gradient column chromatography (EtOAc-Hex 4:1 to MeOH-EtOAc 1:100). The product fractions were collected and concentrated. The solid residue was triturated in ethyl acetate yielding 1-(2-{2-amino-5-[2-(3-hydroxypropyl)-2H-tetrazol-5-yl]pyridin-3-yl}-1-benzothien-5-yl)-3-[4-chloro-3-(trifluoromethyl)phenyl]urea as a white solid in the amount of 50 mg.

$^1$H NMR (600 MHz, DMSO-$d_6$) δ ppm 9.21 (s, 1H) 9.01 (s, 1H) 8.68 (d, J=2.05 Hz, 1H) 8.16 (d, J=2.05 Hz, 1H) 8.13 (d, J=1.76 Hz, 1H) 8.09 (d, J=2.05 Hz, 1H) 7.91 (d, J=8.51 Hz, 1H) 7.69 (s, 1H) 7.64-7.67 (m, 1H) 7.61-7.64 (m, 1H) 7.41 (dd, J=8.66, 1.91 Hz, 1H) 6.68 (s, 2H) 4.76 (t, J=7.04 Hz, 2H) 4.70 (t, J=4.99 Hz, 1H) 3.47 (q, J=5.67 Hz, 2H) 2.11 (quin, J=6.60 Hz, 2H)

Compound 4

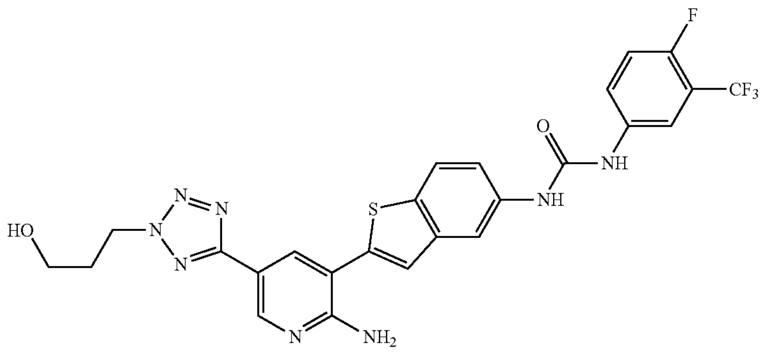 [SMILES: Nc1ncc(-c2nnn(CCCO)n2)cc1-c1cc2cc(NC(=O)Nc3ccc(F)c(C(F)(F)F)c3)ccc2s1]

1-(2-{2-amino-5-[2-(3-hydroxypropyl)-2H-tetrazol-5-yl]pyridin-3-yl}-1-benzothien-5-yl)-3-[4-fluoro-3-(trifluoromethyl)phenyl]urea Synthesized using a procedure similar to the one used for the synthesis of Compound 3.

$^1$H NMR (600 MHz, DMSO-$d_6$) δ ppm 9.06 (s, 1H) 8.95 (s, 1H) 8.68 (s, 1H) 8.11 (d, J=17.61 Hz, 2H) 8.05 (d, J=4.40 Hz, 1H) 7.90 (d, J=8.80 Hz, 1H) 7.69 (s, 1H) 7.63-7.68 (m, 1H) 7.45 (t, J=9.68 Hz, 1H) 7.41 (d, J=8.51 Hz, 1H) 6.68 (br. s., 2H) 4.76 (t, J=6.90 Hz, 2H) 4.70 (t, J=4.84 Hz, 1H) 3.47 (q, J=5.58 Hz, 2H) 2.11 (quin, J=6.46 Hz, 2H).

Compound 5

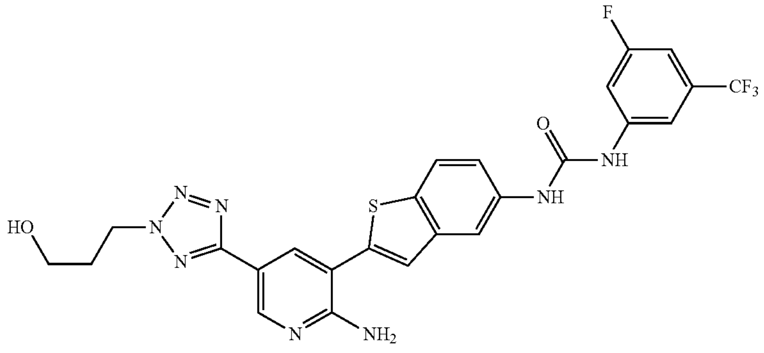 [SMILES: Nc1ncc(-c2nnn(CCCO)n2)cc1-c1cc2cc(NC(=O)Nc3cc(F)cc(C(F)(F)F)c3)ccc2s1]

1-(2-{2-amino-5-[2-(3-hydroxypropyl)-2H-tetrazol-5-yl]pyridin-3-yl}-1-benzothien-5-yl)-3-[3-fluoro-5-(trifluoromethyl)phenyl]urea Synthesized using a procedure similar to the one used for the synthesis of Compound 3.

$^1$H NMR (600 MHz, DMSO-$d_6$) δ ppm 9.30 (br. s., 1H) 9.09 (br. s., 1H) 8.68 (d, J=0.88 Hz, 1H) 8.13 (s, 1H) 8.09 (s, 1H) 7.92 (d, J=8.66 Hz, 1H) 7.75 (s, 1H) 7.70 (s, 1H) 7.64 (d, J=11.15 Hz, 1H) 7.42 (d, J=8.51 Hz, 1H) 7.23 (d, J=8.22 Hz, 1H) 6.68 (br. s., 2H) 4.76 (t, J=6.90 Hz, 2H) 4.70 (t, J=4.84 Hz, 1H) 3.47 (q, J=5.53 Hz, 2H) 2.11 (quin, J=6.35 Hz, 2H).

Compound 6

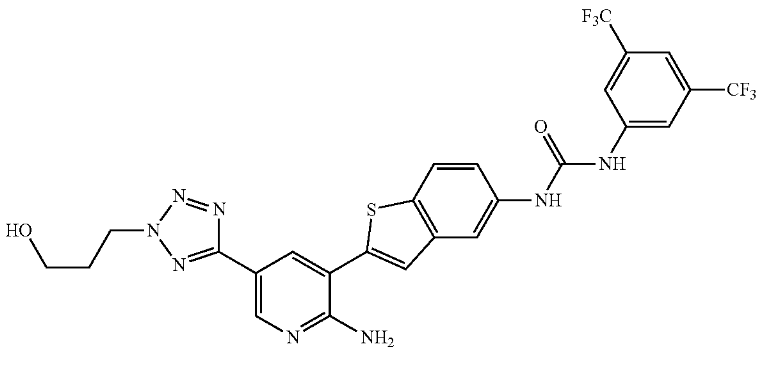 [SMILES: Nc1ncc(-c2nnn(CCCO)n2)cc1-c1cc2cc(NC(=O)Nc3cc(C(F)(F)F)cc(C(F)(F)F)c3)ccc2s1]

1-(2-{2-amino-5-[2-(3-hydroxypropyl)-2H-tetrazol-5-yl]pyridin-3-yl}-1-benzothien-5-yl)-3-[3,5-bis(trifluoromethyl)phenyl]urea Synthesized using a procedure similar to the one used for the synthesis of Compound 3.

$^1$H NMR (600 MHz, DMSO-$d_6$) δ ppm 9.46 (br. s., 1H) 9.18 (br. s., 1H) 8.68 (d, J=1.47 Hz, 1H) 8.17 (s, 2H) 8.15 (s, 1H) 8.10 (d, J=1.17 Hz, 1H) 7.92 (d, J=8.80 Hz, 1H) 7.70 (s, 1H) 7.65 (s, 1H) 7.44 (d, J=8.51 Hz, 1H) 6.68 (br. s., 2H) 4.76 (t, J=6.90 Hz, 2H) 4.70 (t, J=4.84 Hz, 1H) 3.47 (q, J=5.77 Hz, 2H) 2.11 (quin, J=6.46 Hz, 2H)

Compound 7

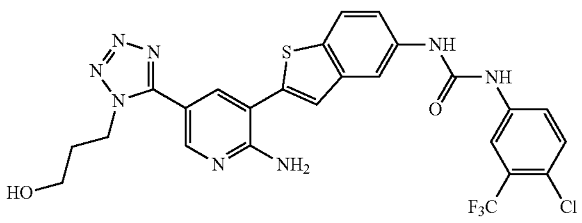 [SMILES: Nc1ncc(-c2nnnn2CCCO)cc1-c1cc2cc(NC(=O)Nc3ccc(Cl)c(C(F)(F)F)c3)ccc2s1]

1-(2-{2-amino-5-[1-(3-hydroxypropyl)-1H-tetrazol-5-yl]pyridin-3-yl}-1-benzothien-5-yl)-3-[4-chloro-3-(trifluoromethyl)phenyl]urea To the solution of 5-(1-(3-((tert-butyldimethylsilyl)oxy)propyl)-1H-tetrazol-5-yl)-3-iodopyridin-2-amine (184 mg, 0.4 mmol, 1 eq), 2-(4,4,5,5-tetramethyl-1,3,2-dioxaborolan-2-yl)benzo[b]thiophen-5-amine (165 mg, 1.5 eq), and triphenylphosphine (21 mg, 0.2 eq) in dioxane (2 mL) and aqueous sodium carbonate (2M, 0.8 mL, 4 eq) under nitrogen atmosphere, was added palladium diacetate (9 mg, 0.1 eq) and the reaction mixture was vigorously stirred at 40° C. for two hours. It was then partitioned between ethyl acetate and aqueous ammonium chloride. The organic layer was isolated, further washed with saturated aqueous sodium bicarbonate, brine, and dried with anhydrous sodium sulfate. The upper clear solution was decanted and concentrated down with silica gel. The mixture was subject to a gradient column chromatography (EtOAc-Hex 1:2 to 5:1) to yield 3-(5-aminobenzo[b]thiophen-2-yl)-5-(1-(3-((tert-butyldimethylsilyl)oxy)propyl)-1H-tetrazol-5-yl)pyridin-2-amine as an oil, which solidified in vacuo, in the amount of 127 mg.

$^1$H NMR (600 MHz, DMSO-$d_6$) δ ppm 8.38 (d, J=2.05 Hz, 1H) 7.87 (d, J=2.05 Hz, 1H) 7.58 (d, J=8.66 Hz, 1H) 7.42 (s, 1H) 6.98 (d, J=1.76 Hz, 1H) 6.70-6.77 (m, 3H) 5.13 (s, 2H) 4.54 (t, J=6.97 Hz, 2H) 3.58 (t, J=5.72 Hz, 2H) 2.07 (quin, J=6.35 Hz, 2H) 0.75 (s, 9H) −0.06 (s, 6H)

To the stirring solution of 3-(5-aminobenzo[b]thiophen-2-yl)-5-(1-(3-((tert-butyldimethylsilyl)oxy)propyl)-1H-tetrazol-5-yl)pyridin-2-amine (123 mg, 0.256 mmol, 1 eq) in anhydrous tetrahydrofuran (3 mL) under nitrogen atmosphere was added 4-chloro-3-(trifluoromethyl)phenyl isocyanate (58 mg, 1 eq) and the reaction mixture was stirred at room temperature for three hours. The reaction was then diluted with ethyl acetate, washed sequentially with aqueous ammonium chloride, saturated aqueous sodium bicarbonate, and brine, and dried with anhydrous sodium sulfate. The upper clear solution was decanted and concentrated under reduced pressure and loaded onto silica. The mixture was subject to a gradient column chromatography (EtOAc-Hex 1:5 to 2:1) to give 1-(2-(2-amino-5-(1-(3-((tert-butyldimethylsilyl)oxy)propyl)-1H-tetrazol-5-yl)pyridin-3-yl)benzo[b]thiophen-5-yl)-3-(4-chloro-3-(trifluoromethyl)phenyl)urea as a white solid in the amount of 130 mg.

$^1$H NMR (600 MHz, DMSO-$d_6$) δ ppm 9.19 (s, 1H) 8.99 (s, 1H) 8.41 (d, J=2.05 Hz, 1H) 8.16 (d, J=2.05 Hz, 1H) 8.14 (d, J=1.47 Hz, 1H) 7.89-7.92 (m, 2H) 7.61-7.67 (m, 3H) 7.40 (dd, J=8.66, 1.91 Hz, 1H) 6.81 (s, 2H) 4.56 (t, J=6.90 Hz, 2H) 3.58 (t, J=5.72 Hz, 2H) 2.08 (quin, J=6.31 Hz, 2H) 0.76 (s, 9H) −0.06 (s, 6H)

To the solution of 1-(2-(2-amino-5-(1-(3-((tert-butyldimethylsilyl)oxy)propyl)-1H-tetrazol-5-yl)pyridin-3-yl)benzo[b]thiophen-5-yl)-3-(4-chloro-3-(trifluoromethyl)phenyl)urea (120 mg, 0.17 mmol, 1 eq) in anhydrous tetrahydrofuran (3 mL) under nitrogen atmosphere at 0° C. was added dropwise a solution of tetrabutylammonium fluoride (1.0 M in THF, 0.51 mL, 3 eq). After the reaction was stirred at room temperature for 2 hours, it was partitioned between ethyl acetate and aqueous ammonium chloride. The organic layer was isolated, further washed with saturated aqueous sodium bicarbonate, brine, and dried with anhydrous sodium sulfate. The upper clear solution was decanted and concentrated and loaded onto silica. The mixture was subject to a gradient column chromatography (EtOAc-Hex 4:1 to MeOH-EtOAc 1:25) to yield 1-(2-{2-amino-5-[1-(3-hydroxypropyl)-1H-tetrazol-5-yl]pyridin-3-yl}-1-benzothien-5-yl)-3-[4-chloro-3-(trifluoromethyl)phenyl]urea as a white solid in the amount of 63 mg.

$^1$H NMR (600 MHz, DMSO-$d_6$) δ ppm 9.20 (s, 1H) 9.00 (s, 1H) 8.44 (d, J=2.20 Hz, 1H) 8.16 (d, J=2.05 Hz, 1H) 8.14 (d, J=1.61 Hz, 1H) 7.96 (d, J=2.05 Hz, 1H) 7.91 (d, J=8.66 Hz, 1H) 7.68 (s, 1H) 7.61-7.67 (m, 2H) 7.40 (dd, J=8.66, 1.91 Hz, 1H) 6.81 (s, 2H) 4.69 (t, J=4.99 Hz, 1H) 4.55 (t, J=7.26 Hz, 2H) 3.44 (q, J=5.58 Hz, 2H) 2.03 (quin, J=6.53 Hz, 2H)

Compound 8

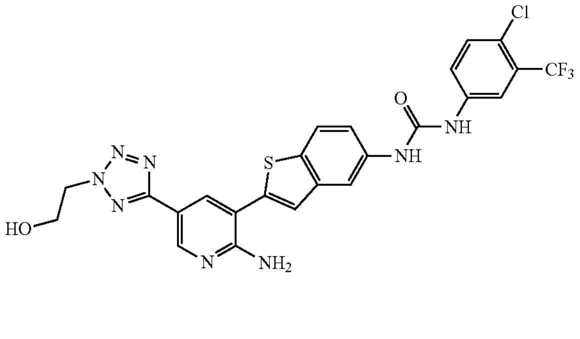 [SMILES: Nc1ncc(-c2nnn(CCO)n2)cc1-c1cc2cc(NC(=O)Nc3ccc(Cl)c(C(F)(F)F)c3)ccc2s1]

1-(2-{2-amino-5-[2-(2-hydroxyethyl)-2H-tetrazol-5-yl]pyridin-3-yl}-1-benzothien-5-yl)-3-[4-chloro-3-(trifluoromethyl)phenyl]urea To the stirring mixture of 3-(5-aminobenzo[b]thiophen-2-yl)-5-isocyanopyridin-2-amine (1.064 g, 4 mmol, 1 eq) in anhydrous tetrahydrofuran (25 mL) under nitrogen atmosphere was added 4-chloro-3-(trifluoromethyl)phenyl isocyanate (904 mg, 1 eq) and the reaction mixture was stirred at room temperature for three hours. The reaction was then diluted with ethyl acetate, washed sequentially with aqueous ammonium chloride, saturated aqueous sodium bicarbonate, and brine, and dried with anhydrous sodium sulfate. The upper clear solution was decanted and concentrated under reduced pressure to lesser amount, to which was added a small amount of EtOAc-Hex (2:1). Upon a filtration, 1-(2-(2-amino-5-isocyanopyridin-3-yl)benzo[b]thiophen-5-yl)-3-(4-chloro-3-(trifluoromethyl)phenyl)urea was obtained as white solid in the amount of 1.37 g.

$^1$H NMR (600 MHz, DMSO-$d_6$) δ ppm 9.23 (s, 1H) 9.03 (s, 1H) 8.42 (d, J=2.05 Hz, 1H) 8.16 (d, J=2.05 Hz, 1H) 8.13 (d, J=1.76 Hz, 1H) 7.89-7.92 (m, 2H) 7.64-7.67 (m, 1H) 7.60-7.64 (m, 2H) 7.40 (dd, J=8.80, 1.76 Hz, 1H) 7.15 (br. s., 2H)

The mixture of 1-(2-(2-amino-5-isocyanopyridin-3-yl)benzo[b]thiophen-5-yl)-3-(4-chloro-3-(trifluoromethyl)phenyl)urea (1.3 g, 2.67 mmol, 1 eq), ammonium chloride (286 mg, 2 eq), and sodium azide (347 mg, 2 eq) in anhydrous dimethylformamide (8 mL) was stirred and heated to 120° C. under nitrogen atmosphere for 2 hours. The mixture was then cooled to room temperature and additional ammonium chloride (286 mg, 2 eq) and sodium azide (347 mg, 2 eq) were added. The reaction mixture was heated back to 120° C. and stirred at that temperature for another hour. After it was cooled to room temperature, it was transferred into ethyl acetate and aqueous ammonium chloride; during the process, the pH of the aqueous layer was adjusted to ~3.5 by using aq $KHSO_4$ (10%). The organic layer was isolated, washed once with saturated brine, and dried with anhydrous sodium sulfate. The upper solution was decanted and concentrated and loaded onto silica. Upon gradient column chromatography (from EtOAc to MeOH-EtOAc 1:2), 1-(2-(2-amino-5-(2H-tetrazol-5-yl)pyridin-3-yl)benzo[b]thiophen-5-yl)-3-(4-chloro-3-(trifluoromethyl)phenyl) was obtained as a yellow solid in the amount of 452 mg.

$^1$H NMR (600 MHz, DMSO-$d_6$) δ ppm 9.29 (s, 1H) 9.07 (s, 1H) 8.61 (s, 1H) 8.16 (br. s., 1H) 8.11 (br. s., 2H) 7.91 (d, J=8.51 Hz, 1H) 7.65-7.69 (m, 2H) 7.61-7.64 (m, 1H) 7.41 (d, J=8.22 Hz, 1H) 6.28 (br. s., 2H)

To the mixture of 1-(2-(2-amino-5-(2H-tetrazol-5-yl)pyridin-3-yl)benzo[b]thiophen-5-yl)-3-(4-chloro-3-(trifluoromethyl)phenyl)urea (106 mg, 0.2 mmol, 1 eq) in anhydrous dimethylformamide (2 mL) under nitrogen atmosphere was added potassium carbonate (41.4 mg, 1.5 eq) and (2-bromoethoxy)-tert-butyldimethylsilane (0.06 mL, 1.3 eq). The resulting mixture was stirred and heated at 80° C. for 2 hours. It was then diluted with ethyl acetate, washed sequentially with aqueous ammonium chloride, saturated aqueous sodium bicarbonate, and brine, and dried with anhydrous sodium sulfate. The upper clear solution was decanted and concentrated under reduced pressure with silica gel. Gradient column chromatography (EtOAc-Hex from 1:100 to 3:1) gave 1-(2-(2-amino-5-(2-(2-((tert-butyldimethylsilyl)oxy)ethyl)-2H-tetrazol-5-yl)pyridin-3-yl)benzo[b]thiophen-5-yl)-3-(4-chloro-3-(trifluoromethyl)phenyl)urea as a fluffy white solid in the amount of 77 mg.

$^1$H NMR (600 MHz, DMSO-$d_6$) δ ppm 9.21 (s, 1H) 9.01 (s, 1H) 8.68 (d, J=2.05 Hz, 1H) 8.17 (d, J=1.76 Hz, 1H) 8.13 (d, J=1.17 Hz, 1H) 8.09 (d, J=2.05 Hz, 1H) 7.91 (d, J=8.51 Hz, 1H) 7.70 (s, 1H) 7.64-7.67 (m, 1H) 7.61-7.64 (m, 1H) 7.41 (dd, J=8.51, 1.76 Hz, 1H) 6.69 (s, 2H) 4.81 (t, J=4.99 Hz, 2H) 4.13 (t, J=4.84 Hz, 2H) 0.73 (s, 9H) −0.10 (s, 6H)

To the solution of 1-(2-(2-amino-5-(2-(2-((tert-butyldimethylsilyl)oxy)ethyl)-2H-tetrazol-5-yl)pyridin-3-yl)benzo[b]thiophen-5-yl)-3-(4-chloro-3-(trifluoromethyl)phenyl)urea (60 mg, 0.087 mmol, 1 eq) in anhydrous tetrahydrofuran (2 mL) under nitrogen atmosphere at 0° C. was added dropwise a solution of tetrabutylammonium fluoride (1.0 M in THF, 0.26 mL, 3 eq). After the reaction was stirred at room temperature for 2 hours, it was partitioned between ethyl acetate and aqueous ammonium chloride. The organic layer was isolated, further washed with saturated aqueous sodium bicarbonate, brine, and dried with anhydrous sodium sulfate. The upper clear solution was decanted and concentrated down with silica gel. The mixture was subject to a gradient column chromatography (EtOAc-Hex 4:1 to MeOH-EtOAc 1:25) to yield 1-(2-{2-amino-5-[2-(2-hydroxyethyl)-2H-tetrazol-5-yl]pyridin-3-yl}-1-benzothien-5-yl)-3-[4-chloro-3-(trifluoromethyl)phenyl]urea as a white solid in the amount of 11 mg.

$^1$H NMR (600 MHz, DMSO-$d_6$) δ ppm 9.26 (br. s., 1H) 9.06 (br. s., 1H) 8.69 (d, J=2.05 Hz, 1H) 8.17 (d, J=2.05 Hz, 1H) 8.13 (d, J=1.47 Hz, 1H) 8.10 (d, J=1.91 Hz, 1H) 7.91 (d, J=8.66 Hz, 1H) 7.70 (s, 1H) 7.64-7.67 (m, 1H) 7.61-7.64 (m, 1H) 7.41 (dd, J=8.66, 1.76 Hz, 1H) 6.68 (s, 2H) 5.07 (t, J=5.65 Hz, 1H) 4.73 (t, J=5.21 Hz, 2H) 3.95 (q, J=5.43 Hz, 2H)

Intermediate 3

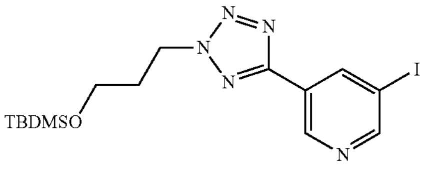 [SMILES: CC(C)(C)[Si](C)(C)OCCCn1nnc(-c2cncc(I)c2)n1]

3-(2-(3-((tert-butyldimethylsilyl)oxy)propyl)-2H-tetrazol-5-yl)-5-iodopyridine

To the reaction mixture of 5-bromo-3-cyanopyridine (3 g, 15.9 mmol, 1 eq), sodium iodide (4.77 g, 2 eq), copper(I) iodide (303 mg, 0.1 eq) in anhydrous 1,4-dioxane (40 mL) under nitrogen atmosphere was added trans-N,N'-dimethyl-cyclohexane-1,2-diamine (0.52 mL, 0.2 eq). After the reaction mixture was heated at 120° C. for 16 hours, it was cooled to room temperature and partitioned between aqueous ammonium chloride and ethyl acetate. The organic layer was isolated, washed with saturated aqueous sodium bicarbonate, brine, and dried with anhydrous sodium chloride. The upper clear solution was decanted, concentrated, and the brown oily residue was subject to a column chromatography (EtOAc-Hex 1:15 to 1:4) yielding 3-iodo-5-isocyanopyridine as a white solid in the amount of 2.41 g.

$^1$H NMR (600 MHz, DMSO-$d_6$) δ ppm 9.11 (d, J=2.05 Hz, 1H) 9.01 (d, J=1.76 Hz, 1H) 8.78 (t, J=2.05 Hz, 1H)

To a solution of 3-iodo-5-isocyanopyridine (2.4 g, 10.43 mmol, 1 eq) in anhydrous DMF (25 mL) in a round bottom flask was added ammonium chloride (0.95 g, 1.7 eq) and sodium azide (1.15 g, 1.7 eq). After the reaction mixture was heated and stirred at 100° C. under anhydrous nitrogen atmosphere for 16 hours, it was cooled to room temperature and poured into ice water. 2 N HCl was dropwise added to adjust the pH ~3 followed by a further stirring for about 30 minutes. The aqueous layer was first extracted with ethyl acetate, followed by an extraction with THF-EtOAc (1:9), and lastly an extraction with i-PrOH—$CHCl_3$ (1:6). All organic solvents were combined and dried with anhydrous sodium sulfate. The upper clear liquor was decanted, concentrated, and the resulting solid residue was treated with EtOAc-Hex (1:9). After the mixture was stirred about 16 hours, it was filtered to yield 3-iodo-5-(2H-tetrazol-5-yl)pyridine as white solid in the amount of 2.36 g.

$^1$H NMR (600 MHz, DMSO-$d_6$) δ ppm 9.18 (d, J=2.05 Hz, 1H) 9.01 (d, J=2.05 Hz, 1H) 8.73 (t, J=1.91 Hz, 1H)

The reaction mixture of 3-iodo-5-(2H-tetrazol-5-yl)pyridine (273 mg, 1 mmol, 1 eq), (3-bromopropoxy)-tert-butyldimethylsilane (0.31 mL, 1.3 eq), potassium carbonate (207 mg, 1.5 eq) in anhydrous DMF (4 mL) under nitrogen atmosphere was stirred and heated at 80° C. for 5 hours. The mixture was then diluted with ethyl acetate, washed sequentially with saturated aqueous sodium bicarbonate, aqueous ammonium chloride, brine, and dried with anhydrous sodium sulfate. The upper liquor was decanted, concentrated under reduced pressure, and the resulting brown oily residue was subject to a gradient column chromatography (EtOAc-Hex 1:50 to 1:4) giving 3-(2-(3-((tert-butyldimethylsilyl)oxy)propyl)-2H-tetrazol-5-yl)-5-iodopyridine as a soft white solid in the amount of 395 mg.

$^1$H NMR (600 MHz, DMSO-$d_6$) δ ppm 9.18 (d, J=1.76 Hz, 1H) 8.98 (d, J=2.05 Hz, 1H) 8.69 (t, J=2.05 Hz, 1H) 4.82 (t, J=6.60 Hz, 2H) 3.65 (t, J=5.87 Hz, 2H) 2.18 (quin, J=6.24 Hz, 2H) 0.84 (s, 9H) 0.00 (s, 6H)

Compound 9

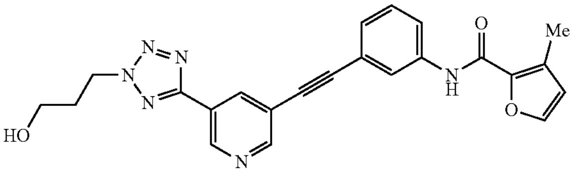 [SMILES: Cc1ccoc1C(=O)Nc1cccc(C#Cc2cncc(-c3nnn(CCCO)n3)c2)c1]

N-[3-({5-[2-(3-hydroxypropyl)-2H-tetrazol-5-yl]pyridin-3-yl}ethynyl)phenyl]-3-methyl-2-furamide To the nitrogen bubbled solution of 3-(2-(3-((tert-butyldimethylsilyl)oxy)propyl)-2H-tetrazol-5-yl)-5-iodopyridine (89 mg, 0.2 mmol, 1 eq), N-(3-ethynylphenyl)-3-methylfuran-2-carboxamide (67.5 mg, 1.5 eq), triphenylphosphine (1.3 mg, 0.025 eq), and triethylamine (0.09 mL, 3 eq) in anhydrous DMF (2 mL) was added bis(triphenylphosphine)palladium(II) dichloride (14 mg, 0.1 eq), and copper(I) iodide (8 mg, 0.2 eq). After the reaction mixture was stirred at room temperature for 20 minutes, it was diluted with ethyl acetate, washed sequentially with saturated aqueous sodium bicarbonate, aqueous ammonium chloride, brine, and dried with anhydrous sodium sulfate. The upper liquor was decanted, concentrated under reduced pressure, and the resulting brown oily residue was loaded onto silica and columned (EtOAc-Hex 1:20 to 1:4). The fractions containing the desired product were collected, concentrated to a lesser amount, and the white fluffy solid was filtered giving N-(3-((5-(2-(3-((tert-butyldimethylsilyl)oxy)propyl)-2H-tetrazol-5-yl)pyridin-3-yl)ethynyl)phenyl)-3-methylfuran-2-carboxamide in an the amount of 78 mg.

$^1$H NMR (600 MHz, DMSO-$d_6$) δ ppm 10.22 (s, 1H) 9.21 (d, J=2.05 Hz, 1H) 8.93 (d, J=1.76 Hz, 1H) 8.52 (t, J=2.05 Hz, 1H) 8.16 (t, J=1.61 Hz, 1H) 7.82 (d, J=1.47 Hz, 1H) 7.79-7.81 (m, 1H) 7.41-7.44 (m, 1H) 7.36 (dt, J=7.56, 1.21 Hz, 1H) 6.61 (d, J=1.47 Hz, 1H) 4.84 (t, J=6.60 Hz, 2H) 3.68 (t, J=5.72 Hz, 2H) 2.36 (s, 3H) 2.20 (quin, J=6.31 Hz, 2H) 0.85 (s, 9H) 0.02 (s, 6H)

To the solution of N-(3-((5-(2-(3-((tert-butyldimethylsilyl)oxy)propyl)-2H-tetrazol-5-yl)pyridin-3-yl)ethynyl)phenyl)-3-methylfuran-2-carboxamide (71 mg, 0.131 mmol, 1 eq) in anhydrous THF (2.6 mL) under nitrogen atmosphere at 0° C. was added dropwise a solution of tetrabutylammonium fluoride (1.0 M in THF, 0.393 mL, 3 eq). The clear reaction solution was stirred at 0° C. using an ice-bath for 3 hours. The solution was then partitioned between ethyl acetate and saturated aqueous sodium bicarbonate. The organic layer was isolated, washed with aqueous ammonium chloride, brine, and dried with anhydrous sodium sulfate. The upper clear liquor was decanted, concentrated, and the oily residue was loaded onto silica and chromatographed (EtOAc-Hex 1:4 to 4:1) to yield N-[3-({5-[2-(3-hydroxypropyl)-2H-tetrazol-5-yl]pyridin-3-yl}ethynyl)phenyl]-3-methyl-2-furamide as a white solid in the amount of 28 mg.

$^1$H NMR (600 MHz, DMSO-$d_6$) δ ppm 10.22 (s, 1H) 9.22 (d, J=2.05 Hz, 1H) 8.94 (d, J=2.05 Hz, 1H) 8.53 (t, J=2.05 Hz, 1H) 8.16 (t, J=1.76 Hz, 1H) 7.82 (d, J=1.47 Hz, 1H) 7.79-7.82 (m, 1H) 7.41-7.44 (m, 1H) 7.37 (dt, J=7.63, 1.17 Hz, 1H) 6.61

(d, J=1.47 Hz, 1H) 4.84 (t, J=7.04 Hz, 2H) 4.72 (t, J=4.99 Hz, 1H) 3.49 (q, J=5.87 Hz, 2H) 2.36 (s, 3H) 2.15 (quin, J=6.60 Hz, 2H)

Compound 10

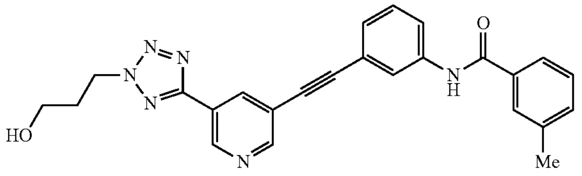 [SMILES: Cc1cccc(C(=O)Nc2cccc(C#Cc3cncc(-c4nnn(CCCO)n4)c3)c2)c1]

N-[3-({5-[2-(3-hydroxypropyl)-2H-tetrazol-5-yl]pyridin-3-yl}ethynyl)phenyl]-3-methylbenzamide Synthesized using a procedure similar to the one used for the synthesis of Compound 9.

$^1$H NMR (600 MHz, DMSO-$d_6$) δ ppm 10.35 (s, 1H) 9.22 (d, J=2.05 Hz, 1H) 8.94 (d, J=1.76 Hz, 1H) 8.54 (t, J=2.05 Hz, 1H) 8.14 (t, J=1.76 Hz, 1H) 7.82-7.84 (m, 1H) 7.79 (s, 1H) 7.75-7.78 (m, 1H) 7.41-7.48 (m, 3H) 7.39 (dt, J=7.63, 1.17 Hz, 1H) 4.84 (t, J=7.04 Hz, 2H) 4.72 (t, J=4.99 Hz, 1H) 3.49 (q, J=5.87 Hz, 2H) 2.41 (s, 3H) 2.15 (quin, J=6.53 Hz, 2H)

Compound 11

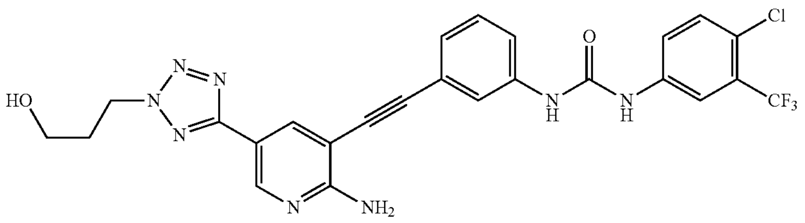 [SMILES: Nc1ncc(-c2nnn(CCCO)n2)cc1C#Cc1cccc(NC(=O)Nc2ccc(Cl)c(C(F)(F)F)c2)c1]

1-[3-({2-amino-5-[2-(3-hydroxypropyl)-2H-tetrazol-5-yl]pyridin-3-yl}ethynyl)phenyl]-3-[4-chloro-3-(trifluoromethyl)phenyl]urea A mixture of 3-((3-aminophenyl)ethynyl)-5-(2-(3-((tert-butyldimethylsilyl)oxy)propyl)-2H-tetrazol-5-yl)pyridin-2-amine (135 mg, 0.3 mmol, 1 eq) and 4-chloro-3-(trifluoromethyl)phenyl isocyanate (67 mg, 1 eq) in anhydrous tetrahydrofuran (3 mL) was stirred at room temperature and under nitrogen atmosphere for 3 hours. The mixture was then diluted with ethyl acetate, washed sequentially with aqueous ammonium chloride, saturated aqueous sodium bicarbonate, and brine, and dried with anhydrous sodium sulfate. The clear solution was decanted, concentrated under reduced pressure, and the resulting clear oil was dried in vacuo for 5 minutes. It was then treated with a small amount of EtoAc-Hex (1:9), followed by stirring at room temperature for 30 minutes. The white solid that appeared during the process was filtered giving 1-(3-((2-amino-5-(2-(3-((tert-butyldimethylsilyl)oxy)propyl)-2H-tetrazol-5-yl)pyridin-3-yl)ethynyl)phenyl)-3-(4-chloro-3-(trifluoromethyl)phenyl)urea in the amount of 201 mg.

$^1$H NMR (600 MHz, DMSO-$d_6$) δ ppm 9.25 (s, 1H) 8.95 (s, 1H) 8.63 (s, 1H) 8.14 (s, 2H) 7.83 (s, 1H) 7.60-7.67 (m, 2H) 7.44 (br. s., 1H) 7.36 (d, J=4.11 Hz, 2H) 6.92 (br. s., 2H) 4.75 (t, J=6.60 Hz, 2H) 3.65 (t, J=5.72 Hz, 2H) 2.16 (quin, J=6.16 Hz, 2H) 0.85 (s, 9H) 0.02 (s, 6H)

To the solution of 1-(3-((2-amino-5-(2-(3-((tert-butyldimethylsilyl)oxy)propyl)-2H-tetrazol-5-yl)pyridin-3-yl)ethynyl)phenyl)-3-(4-chloro-3-(trifluoromethyl)phenyl)urea (188 mg, 0.28 mmol, 1 eq) in anhydrous tetrahydrofuran (5 mL) under nitrogen atmosphere at 0° C. was added dropwise tetrabutylammonium fluoride (1.0 M in THF, 0.84 mL, 3 eq). The reaction was stirred at room temperature for 3 hours and then concentrated and loaded onto silica. The mixture was subject to a column chromatography (EtOAc-Hex 4:1 to MeOH-EtOAc 1:25) to yield 1-[3-({2-amino-5-[2-(3-hydroxypropyl)-2H-tetrazol-5-yl]pyridin-3-yl}ethynyl)phenyl]-3-[4-chloro-3-(trifluoromethyl)phenyl]urea as a white solid in the amount of 127 mg.

$^1$H NMR (600 MHz, DMSO-$d_6$) δ ppm 9.26 (s, 1H) 8.96 (s, 1H) 8.64 (s, 1H) 8.14 (d, J=7.04 Hz, 2H) 7.82 (s, 1H) 7.61-7.67 (m, 2H) 7.43-7.46 (m, 1H) 7.34-7.37 (m, 2H) 6.91 (br. s., 2H) 4.75 (t, J=7.04 Hz, 2H) 4.70 (t, J=4.99 Hz, 1H) 3.47 (q, J=5.58 Hz, 2H) 2.11 (quin, J=6.46 Hz, 2H)

Compound 12

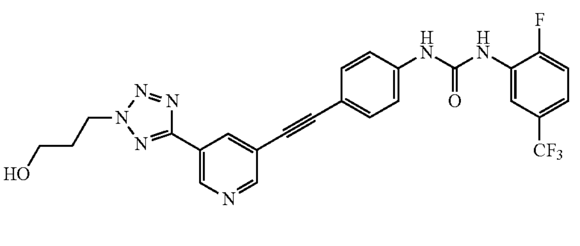 [SMILES: O=C(Nc1ccc(C#Cc2cncc(-c3nnn(CCCO)n3)c2)cc1)Nc1cc(C(F)(F)F)ccc1F]

1-[2-fluoro-5-(trifluoromethyl)phenyl]-3-[4-({5-[2-(3-hydroxypropyl)-2H-tetrazol-5-yl]pyridin-3-yl}ethynyl)phenyl]urea Synthesized using a procedure similar to the one used for the synthesis of Compound 11. $^1$H NMR (600 MHz, DMSO-$d_6$) δ ppm 9.43 (s, 1H) 9.19 (d, J=1.47 Hz, 1H) 8.98 (d, J=2.05 Hz, 1H) 8.89 (d, J=1.47 Hz, 1H) 8.61 (dd, J=7.04, 1.47 Hz, 1H) 8.49 (s, 1H) 7.56-7.61 (m, 4H) 7.51 (dd, J=10.12, 9.24 Hz, 1H) 7.42 (dt, J=7.92, 3.67 Hz, 1H) 4.84 (t, J=7.04 Hz, 2H) 4.72 (t, J=4.99 Hz, 1H) 3.49 (q, J=5.87 Hz, 2H) 2.15 (quin, J=6.53 Hz, 2H).

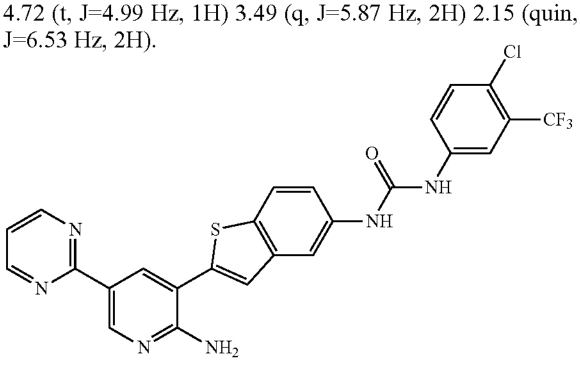

Compound 13

1-[2-(2-amino-5-pyrimidin-2-ylpyridin-3-yl)-1-benzothien-5-yl]-3-[4-chloro-3-(trifluoromethyl)phenyl]urea 1-{2-[2-amino-5-(4,4,5,5-tetramethyl-1,3,2-dioxaborolan-2-yl)pyridin-3-yl]-1-benzothien-5-yl}-3-[4-chloro-3-(trifluoromethyl)phenyl]urea (194 mg, 0.33 mmoles) and 2-chloropyrimidine (38 mg, 0.3 mmoles) was added to a mixture of 6 ml of dioxane and 2 ml of 2M aqueous Sodium Carbonate. Next, Palladium(II) Acetate (10 mol %, 7 mg) and Triphenylphosphene (20 mol %, 16 mg) was added, followed by 2 ml of dioxane. Dry nitrogen was bubbled through the resulting solution for 15 minutes. Following this, the reaction mixture was set up with a reflux condenser, under nitrogen atmosphere, and heated at 95 C overnight. The reaction was then cooled to room temperature and 40 ml of ethyl acetate was added. The mixture was transferred to a separatory funnel and extracted with saturated Sodium Bicarbonate (3×40 ml) followed by saturated NaCl (3×40 ml). The organic layer was dried with anhydrous Sodium Sulfate, loaded onto silica and columned using ethyl acetate/hexanes, to give 30 mg of the product. $^1$H NMR (<dmso>) δ: 9.19 (s, 1H), 9.02 (d, J=2.1 Hz, 1H), 8.99 (s, 1H), 8.83 (d, J=4.7 Hz, 2H), 8.47 (d, J=2.1 Hz, 1H), 8.14 (dd, J=13.8, 2.1 Hz, 2H), 7.90 (d, J=8.8 Hz, 1H), 7.68 (s, 1H), 7.58-7.66 (m, 2H), 7.41 (dd, J=8.8, 2.1 Hz, 1H), 7.35 (t, J=4.8 Hz, 1H), 6.71 (s, 2H).

Compound 14

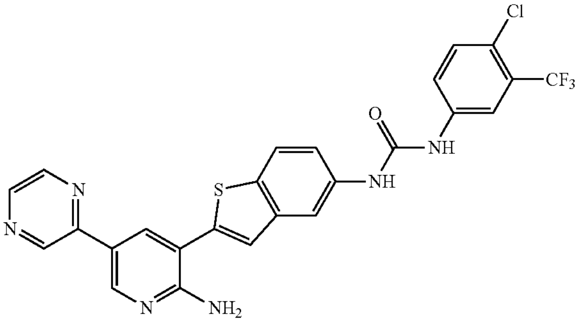 [SMILES: Nc1ncc(-c2cnccn2)cc1-c1cc2cc(NC(=O)Nc3ccc(Cl)c(C(F)(F)F)c3)ccc2s1]

1-[2-(2-amino-5-pyrazin-2-ylpyridin-3-yl)-1-benzothien-5-yl]-3-[4-chloro-3-(trifluoromethyl)phenyl]urea Synthesized using a procedure similar to Example 13.

$^1$H NMR (<dmso>) δ: 9.24 (d, J=1.5 Hz, 1H), 9.20-9.23 (m, 1H), 9.00 (s, 1H), 8.83 (d, J=2.3 Hz, 1H), 8.64 (dd, J=2.5, 1.6 Hz, 1H), 8.51 (d, J=2.3 Hz, 1H), 8.30 (d, J=2.3 Hz, 1H), 8.16 (d, J=2.3 Hz, 1H), 8.12 (d, J=2.1 Hz, 1H), 7.91 (d, J=8.8 Hz, 1H), 7.59-7.72 (m, 3H), 7.41 (dd, J=8.6, 2.2 Hz, 1H), 6.61 (s, 2H).

Biological data for the compounds of the present invention was generated by use of the following assays.

VEGFR2 Kinase Assay

Biochemical KDR kinase assays were performed in 96 well microtiter plates that were coated overnight with 75 μg/well of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 2.7 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain KDR protein (BPS Bioscience, San Diego, Calif.). Following a 15 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

PDGFRβ Kinase Assay

Biochemical PDGFRβ kinase assays were performed in 96 well microtiter plates that were coated overnight with 75 μg of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 36 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain PDGFR-b protein (Millipore). Following a 60 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of 0-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

PKR KinaseGlo Assay

Commercially available recombinant human GST-PKR (SignalChem, Canada; 1.5 uM-2 uM stock) is diluted to 500 nM in assay buffer (20 mM Tris-HCl, pH 7.2, 10 mM KCl, 10 mM MgCl2, 10% glycerol). Preactivated PKR is dispensed to 384/96-well black plates at 3.125/12.5 uls/well using the liquid handler Janus. Appropriate dilutions of inhibitors are added to 384/96-well plate followed by 6.6 uM ATP (final) and incubated for 10 minutes at room temperature. The remaining ATP/well is determined by adding 6.25/25 uls/well Kinase-Glo assay mix (Promega) and luminescence is measured on EnVision luminescence plate reader (integration time, 0.2 sec; Perkin-Elmer, Massachusetts, USA). The % inhibition for the compounds is calculated using ATP only (100% inhibition) and PKR+ATP (0% inhibition). 1050 values are determined by plotting % activity versus inhibitor concentration. Curves are fitted using Activity base XLfit (IDBS, UK) using the formula—

4 Parameter Logistic Model $$fit=(A+((B-A)/(1+(10^{\wedge}((C-x)*D)))))$$

$$inv=(C-(\log(((B-A)/(y-A))-1)/D))$$

$$res=(y-fit)$$

The biological results for the various compounds are shown in Table 1 below.

TABLE 1

In vitro VEGFR2 and PDGFRβ data

| Ex. | Structure | VEGFR2 Kinase Assay ($10_{50}$ nM) | PKR KinaseGlo Assay ($10_{50}$ nM) | PDGFRβ Kinase Assay ($10_{50}$ nM) |
|---|---|---|---|---|
| 1 | 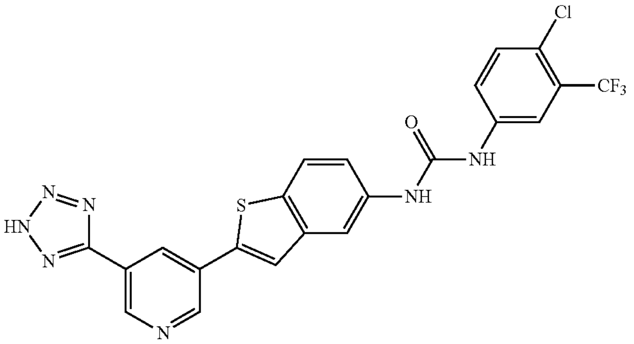 [SMILES: O=C(Nc1ccc(Cl)c(C(F)(F)F)c1)Nc1ccc2sc(-c3cncc(-c4nn[nH]n4)c3)cc2c1] | na | 727 | na |
| 2 | 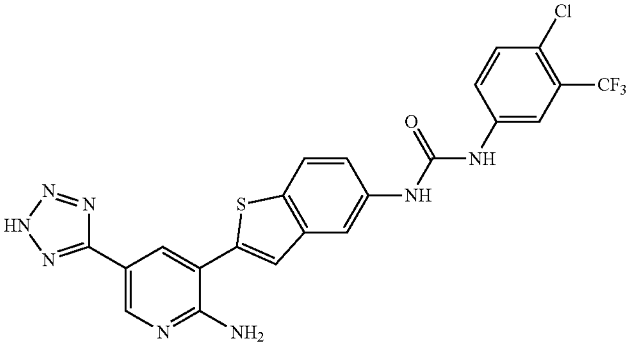 [SMILES: Nc1ncc(-c2nn[nH]n2)cc1-c1cc2cc(NC(=O)Nc3ccc(Cl)c(C(F)(F)F)c3)ccc2s1] | na | 140 | na |
| 3 | 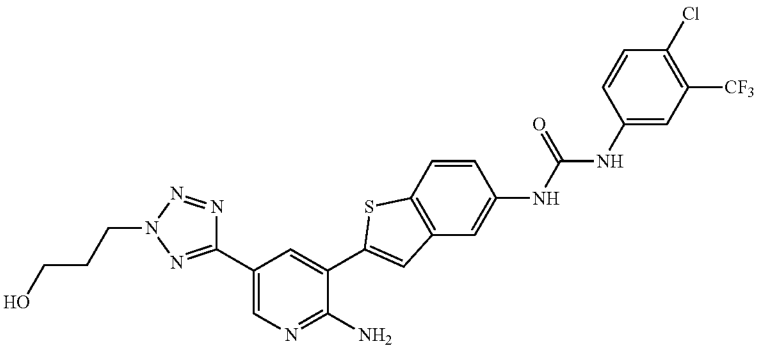 [SMILES: Nc1ncc(-c2nnn(CCCO)n2)cc1-c1cc2cc(NC(=O)Nc3ccc(Cl)c(C(F)(F)F)c3)ccc2s1] | na | 39 | na |

TABLE 1-continued
In vitro VEGFR2 and PDGFRβ data
| Ex. | Structure | VEGFR2 Kinase Assay ($10_{50}$ nM) | PKR KinaseGlo Assay ($10_{50}$ nM) | PDGFRβ Kinase Assay ($10_{50}$ nM) |
| --- | --- | --- | --- | --- |
| 4 | 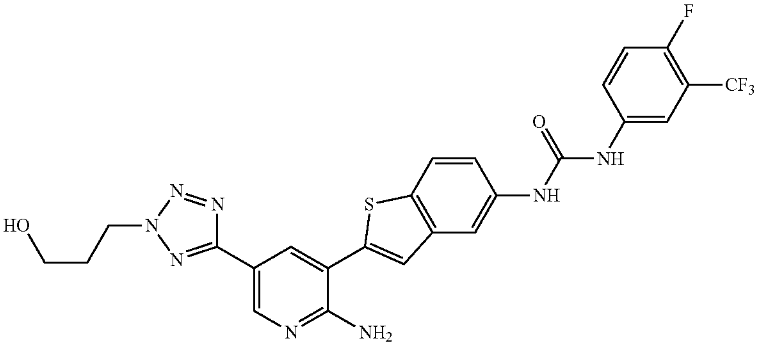 | na | 99 | na |
| 5 | 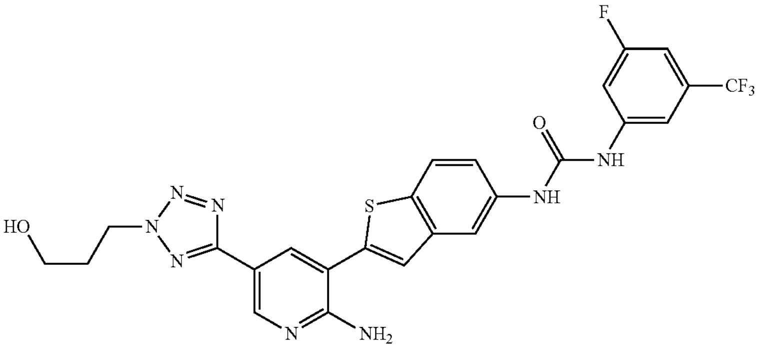 | na | 76 | na |
| 6 | 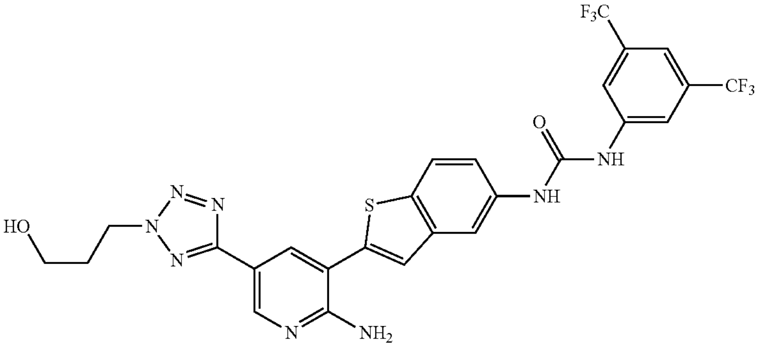 | na | 66 | na |
| 7 | 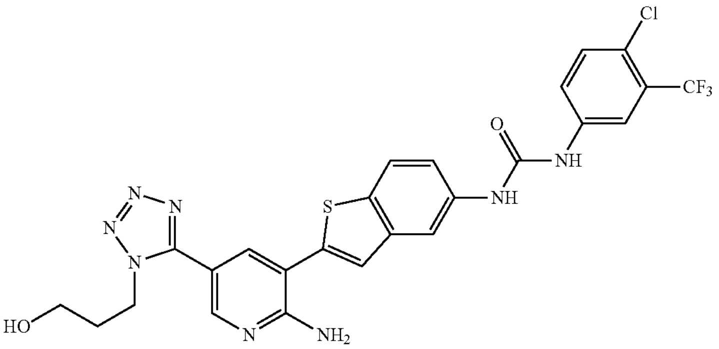 [SMILES: Nc1ncc(-c2nnnn2CCCO)cc1-c1cc2cc(NC(=O)Nc3ccc(Cl)c(C(F)(F)F)c3)ccc2s1] | na | na | na |

TABLE 1-continued
| In vitro VEGFR2 and PDGFRβ data | | | | |
|---|---|---|---|---|
| Ex. | Structure | VEGFR2 Kinase Assay ($10_{50}$ nM) | PKR KinaseGlo Assay ($10_{50}$ nM) | PDGFRβ Kinase Assay ($10_{50}$ nM) |
| 8 | 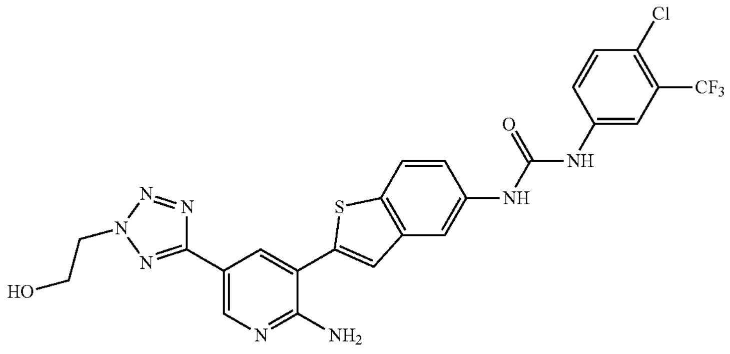 [SMILES: Nc1ncc(-c2nnn(CCO)n2)cc1-c1cc2cc(NC(=O)Nc3ccc(Cl)c(C(F)(F)F)c3)ccc2s1] | na | 82 | na |
| 9 | 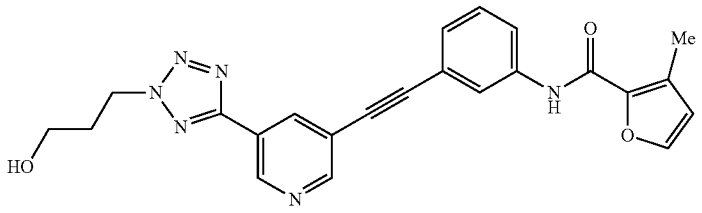 [SMILES: Cc1ccoc1C(=O)Nc1cccc(C#Cc2cncc(-c3nnn(CCCO)n3)c2)c1] | 5 | >10,000 | 21 |
| 10 | 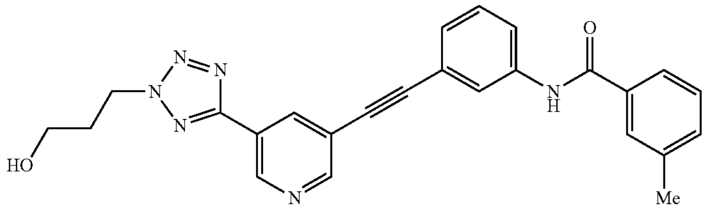 [SMILES: Cc1cccc(C(=O)Nc2cccc(C#Cc3cncc(-c4nnn(CCCO)n4)c3)c2)c1] | 7 | na | na |
| 11 | 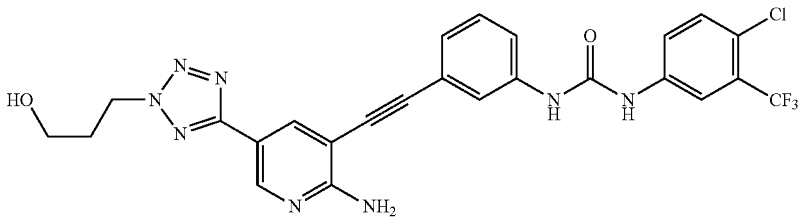 [SMILES: Nc1ncc(-c2nnn(CCCO)n2)cc1C#Cc1cccc(NC(=O)Nc2ccc(Cl)c(C(F)(F)F)c2)c1] | na | 158 | na |
| 12 | 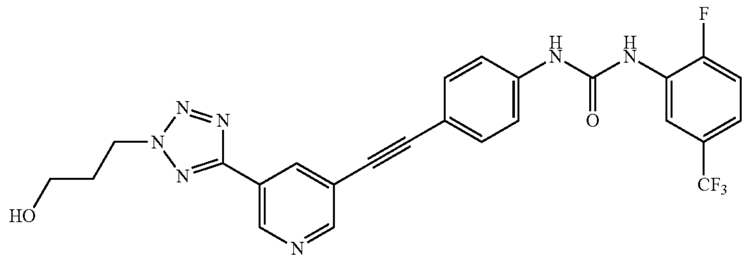 [SMILES: O=C(Nc1ccc(C#Cc2cncc(-c3nnn(CCCO)n3)c2)cc1)Nc1cc(C(F)(F)F)ccc1F] | 8 | >10,000 | na |

TABLE 1-continued

| In vitro VEGFR2 and PDGFRβ data | | | | |
|---|---|---|---|---|
| Ex. | Structure | VEGFR2 Kinase Assay ($10_{50}$ nM) | PKR KinaseGlo Assay ($10_{50}$ nM) | PDGFRβ Kinase Assay ($10_{50}$ nM) |
| 13 | 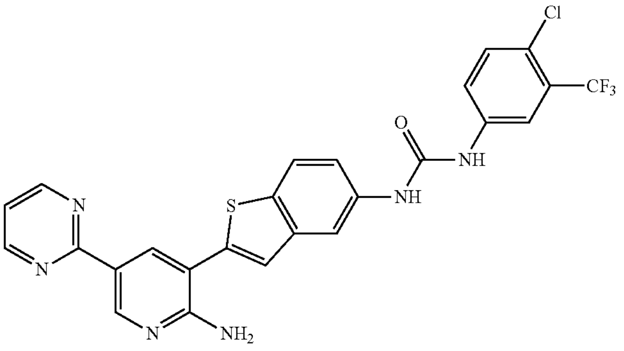 [SMILES: Nc1ncc(-c2ncccn2)cc1-c1cc2cc(NC(=O)Nc3ccc(Cl)c(C(F)(F)F)c3)ccc2s1] | na | 558 | na |
| 14 | 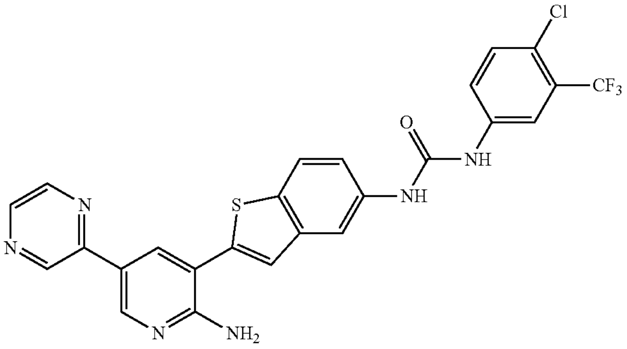 [SMILES: Nc1ncc(-c2cnccn2)cc1-c1cc2cc(NC(=O)Nc3ccc(Cl)c(C(F)(F)F)c3)ccc2s1] | na | 301 | na |

What is claimed is:

1. A compound represented by Formula I, its enantiomers, diastereoisomers, or a pharmaceutically acceptable salt thereof:

Formula I

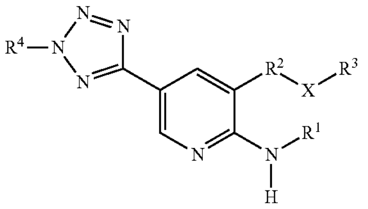

wherein:

$R^1$ is hydrogen;

X is

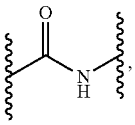, 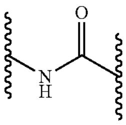 or 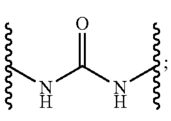 [SMILES: *NC(=O)N*];

$R^2$ is benzothiophene;

$R^3$ is phenyl, optionally substituted with methyl, trifluoromethyl, fluoro, or chloro;

$R^4$ is hydrogen or $C_1$-$C_8$ alkyl optionally substituted with hydroxyl.

2. The compound according to claim 1, wherein:

X is

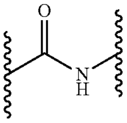.

3. The compound according to claim 1, wherein:

X is

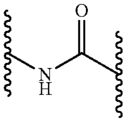.

4. The compound according to claim 1, wherein:

X is

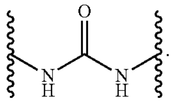

5. The compound according to claim 1, wherein:

$R^1$ is hydrogen;

X is

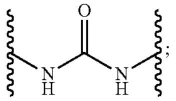

$R^2$ is benzothiophene;

$R^3$ is phenyl optionally substituted with methyl, trifluoromethyl, fluoro, or chloro;

$R^4$ is hydrogen or $C_1$-$C_8$ alkyl optionally substituted with hydroxyl.

6. The compound according to claim 1, wherein:

$R^1$ is hydrogen;

X is

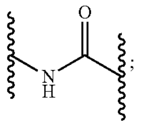 [SMILES: *NC(*)=O]

$R^2$ is benzothiophene;

$R^3$ is phenyl, optionally substituted with methyl, trifluoromethyl, fluoro, or chloro; and $R^4$ is $C_1$-$C_8$ alkyl optionally substituted with hydroxyl.

7. A compound selected from the group consisting of:

1-{2-[2-amino-5-(2H-tetrazol-5-yl)pyridin-3-yl]-1-benzothien-5-yl}-3-[4-chloro-3-(trifluoromethyl)phenyl]urea;

1-(2-{2-amino-5-[2-(3-hydroxypropyl)-2H-tetrazol-5-yl]pyridin-3-yl}-1-benzothien-5-yl)-3-[4-chloro-3-(trifluoromethyl)phenyl]urea;

1-(2-{2-amino-5-[2-(3-hydroxypropyl)-2H-tetrazol-5-yl]pyridin-3-yl}-1-benzothien-5-yl)-3-[4-fluoro-3-(trifluoromethyl)phenyl]urea;

1-(2-{2-amino-5-[2-(3-hydroxypropyl)-2H-tetrazol-5-yl]pyridin-3-yl}-1-benzothien-5-yl)-3-[3-fluoro-5-(trifluoromethyl)phenyl]urea;

1-(2-{2-amino-5-[2-(3-hydroxypropyl)-2H-tetrazol-5-yl]pyridin-3-yl}-1-benzothien-5-yl)-3-[3,5-bis(trifluoromethyl)phenyl]urea; and 1-(2-{2-amino-5-[2-(2-hydroxyethyl)-2H-tetrazol-5-yl]pyridin-3-yl}-1-benzothien-5-yl)-3-[4-chloro-3-(trifluoromethyl)phenyl]urea;

or a pharmaceutically acceptable salt thereof.

8. A pharmaceutical composition comprising as active ingredient a therapeutically effective amount of a compound according to claim 1 and a pharmaceutically acceptable adjuvant, diluent or carrier.

* * * * *